(12) United States Patent
Oglesby et al.

(10) Patent No.: US 8,851,083 B2
(45) Date of Patent: Oct. 7, 2014

(54) DEVICE FOR VAPORISING VAPORISABLE MATTER

(75) Inventors: Alfred Peter Oglesby, Carlingford (IE); John Paul Oglesby, Carlow (IE)

(73) Assignee: Oglesby & Butler Research & Development Limited, Carlow (IE)

( * ) Notice: Subject to any disclaimer, the term of this patent is extended or adjusted under 35 U.S.C. 154(b) by 1842 days.

(21) Appl. No.: 11/815,297

(22) PCT Filed: Feb. 2, 2006

(86) PCT No.: PCT/IE2006/000006
§ 371 (c)(1),
(2), (4) Date: Nov. 2, 2007

(87) PCT Pub. No.: WO2006/082571
PCT Pub. Date: Aug. 10, 2006

(65) Prior Publication Data
US 2008/0149118 A1 Jun. 26, 2008

(30) Foreign Application Priority Data

Feb. 2, 2005 (IE) .................................. S2005/0051
Aug. 24, 2005 (IE) .................................. S2005/0563
Sep. 19, 2005 (IE) .................................. S2005/0615

(51) Int. Cl.
*A24F 47/00* (2006.01)
*A61M 11/04* (2006.01)
*A61M 15/06* (2006.01)

(52) U.S. Cl.
CPC ....... *A61M 15/06* (2013.01); *A61M 2205/3368* (2013.01); *A24F 47/006* (2013.01); *A61M 11/047* (2013.01)
USPC ........................................................ 131/271

(58) Field of Classification Search
CPC ... A24F 47/006; A24F 47/004; A24F 47/002; A61M 11/04; A61M 15/06
See application file for complete search history.

(56) References Cited

U.S. PATENT DOCUMENTS 1,344,698 A * 6/1920 Knight ............................ 165/52
2,668,993 A 2/1954 Bair
(Continued)

FOREIGN PATENT DOCUMENTS

DE 198 54 008 A1 5/2000
DE 19854005 A1 5/2000
(Continued)

OTHER PUBLICATIONS

Machine English translation of DE 19854008.*

*Primary Examiner* — Michael J Felton
(74) *Attorney, Agent, or Firm* — Sughrue Mion, PLLC

(57) ABSTRACT

A device (1) for producing an aerosol from vaporizable constituents of tobacco comprises a vaporizing chamber (24) within which the tobacco is placed. A main housing (9) which forms a portion of the vaporizing chamber also forms a combustion chamber (18) within which a gas catalytic combustion element (19) is located for converting fuel gas to heat by catalytic action. A temperature responsive control valve (61) controls the supply of fuel gas to the combustion chamber for maintaining the temperature in the vaporizing chamber A thermal mass (96) secured to a tab portion (95) of the gas catalytic combustion element maintains the temperature of the tab portion at or above the ignition temperature of the gas catalytic combustion element during periods of fuel gas interruption by the control valve. Vaporised constituents of the tobacco are drawn from the vaporizing chamber through an aerosol accommodating tube (37) through a mouthpiece (38). A heat sink member (40) is located in the aerosol accommodating tube for cooling the aerosol and for condensing tar as the aerosol is drawn from the vaporizing chamber.

21 Claims, 8 Drawing Sheets

(56) References Cited

U.S. PATENT DOCUMENTS

Figure 3:
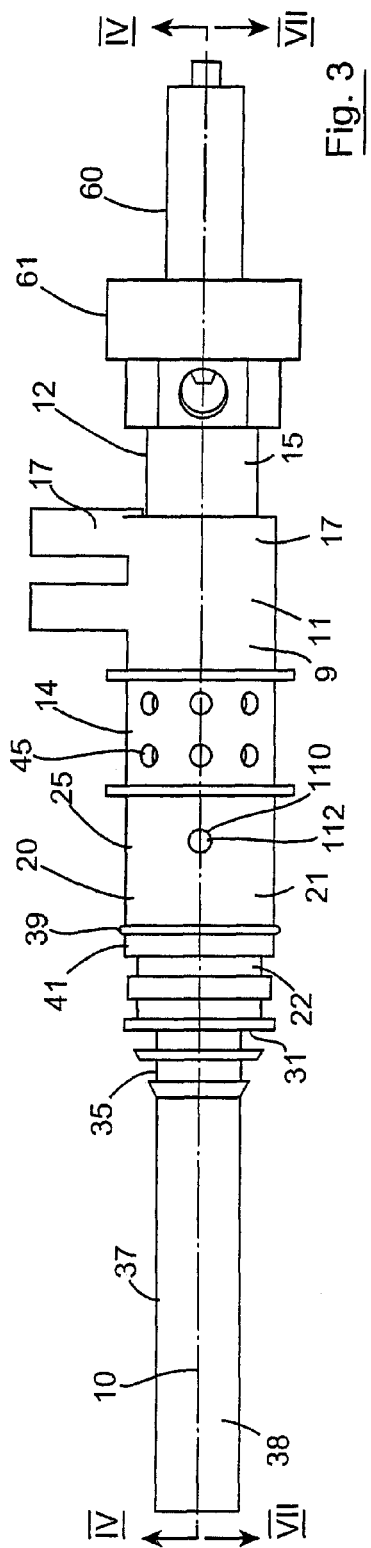

| | | | |
|---|---|---|---|
| 3,270,798 A * | 9/1966 | Ruff | 431/329 |
| 3,425,414 A | 2/1969 | Roche | |
| 4,200,114 A * | 4/1980 | Waite | 131/178 |
| 4,327,752 A * | 5/1982 | Hickel | 132/263 |
| 4,776,353 A | 10/1988 | Lilja et al. | |
| 5,080,114 A | 1/1992 | Rudolph et al. | |
| 5,144,962 A | 9/1992 | Counts et al. | |
| 5,819,756 A | 10/1998 | Mielordt | |
| 5,944,025 A | 8/1999 | Cook et al. | |
| 6,089,857 A * | 7/2000 | Matsuura et al. | 431/142 |
| 6,095,153 A | 8/2000 | Kessler et al. | |
| 2004/0016532 A1 | 1/2004 | Wagner | |
| 2004/0031495 A1 | 2/2004 | Steinberg | |
| 2004/0099266 A1 | 5/2004 | Cross et al. | |
| 2005/0016550 A1 | 1/2005 | Katase | |

FOREIGN PATENT DOCUMENTS

| | | |
|---|---|---|
| EP | 0 893 071 A1 | 1/1999 |
| GB | 19131035 | 7/1913 |
| WO | 95/09712 A1 | 4/1995 |
| WO | 02/48591 A1 | 6/2002 |
| WO | WO 02/056932 A2 | 7/2002 |
| WO | 2006/033091 A1 | 3/2006 |

* cited by examiner

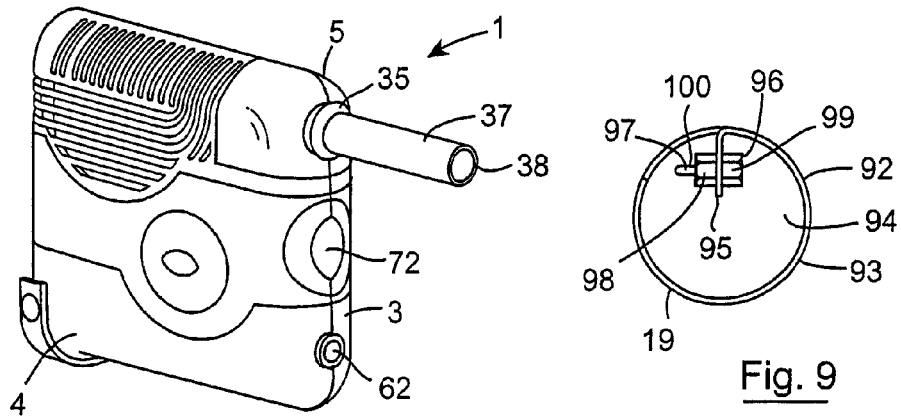
Fig. 1
Fig. 9
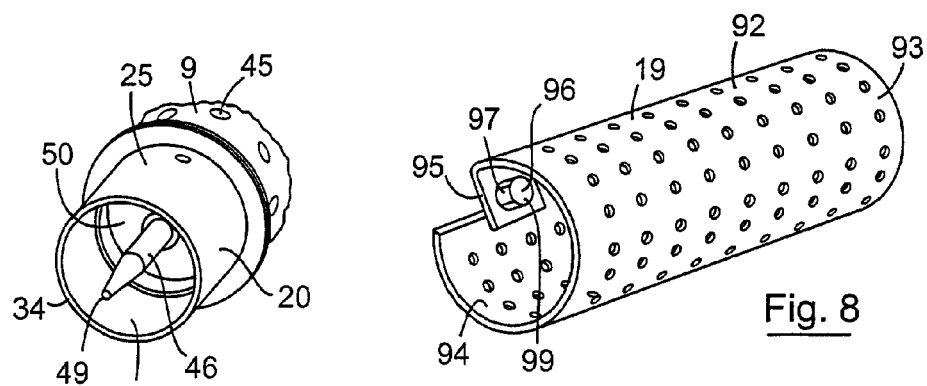
Fig. 5
Fig. 8
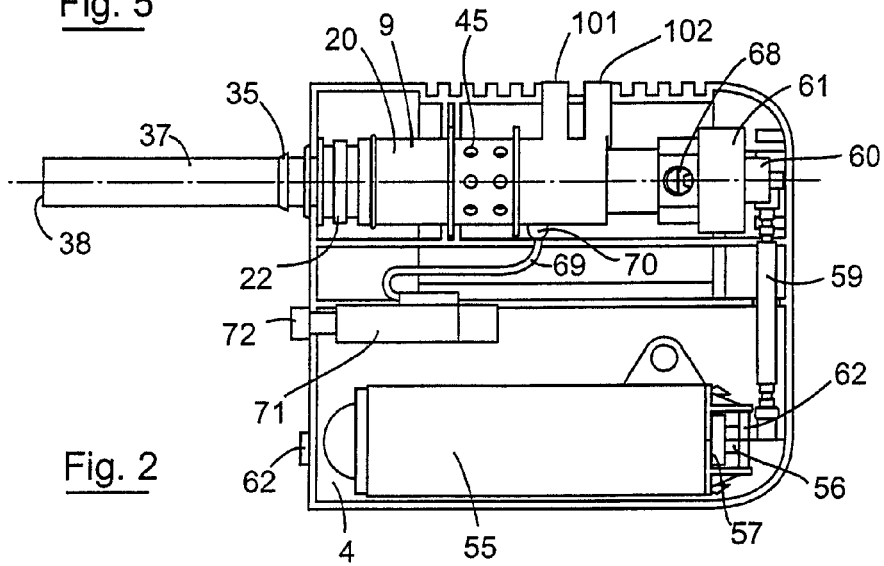
Fig. 2

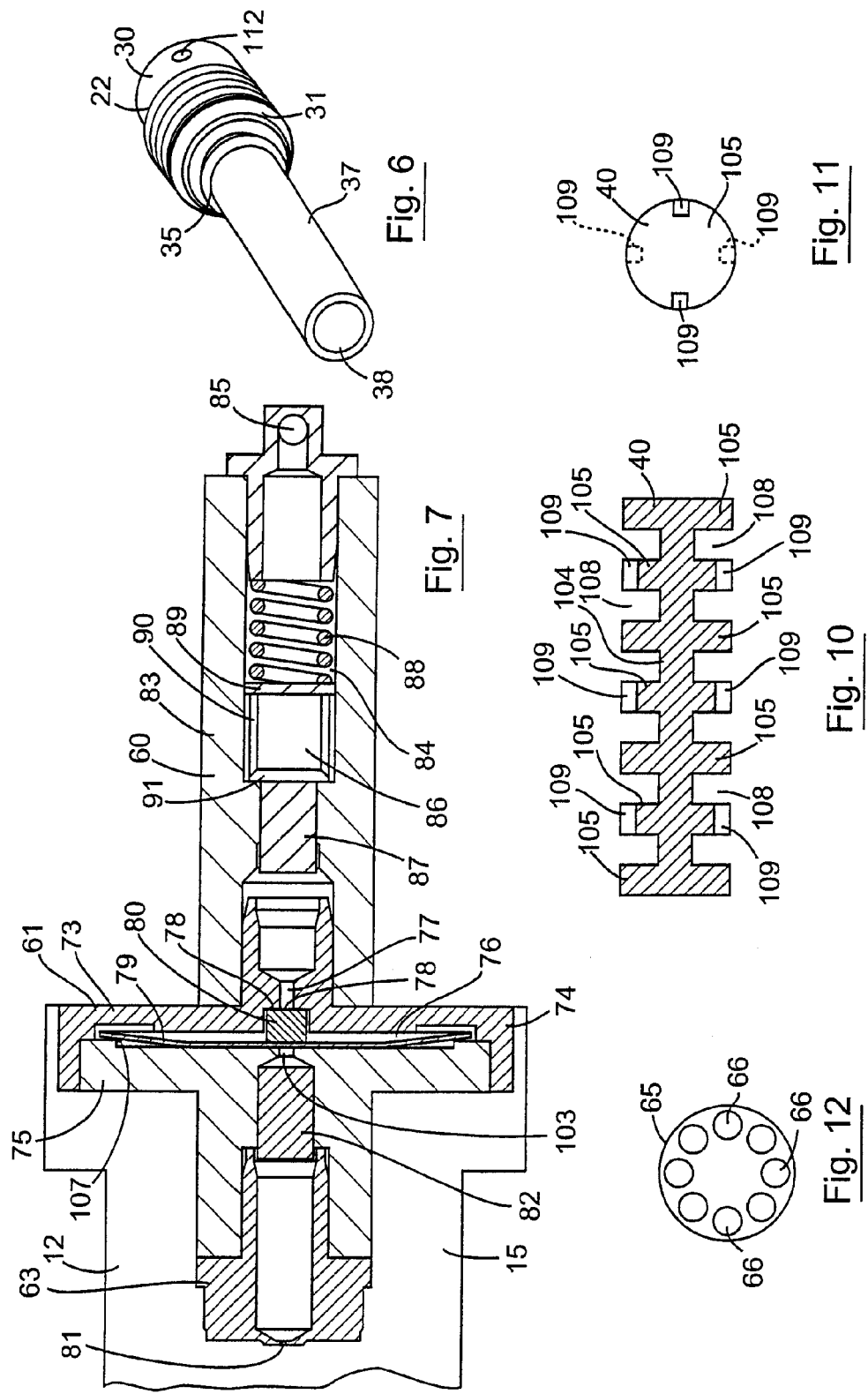

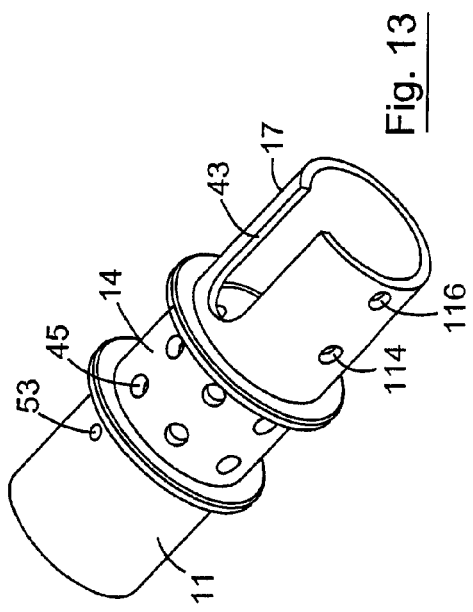
Fig. 13
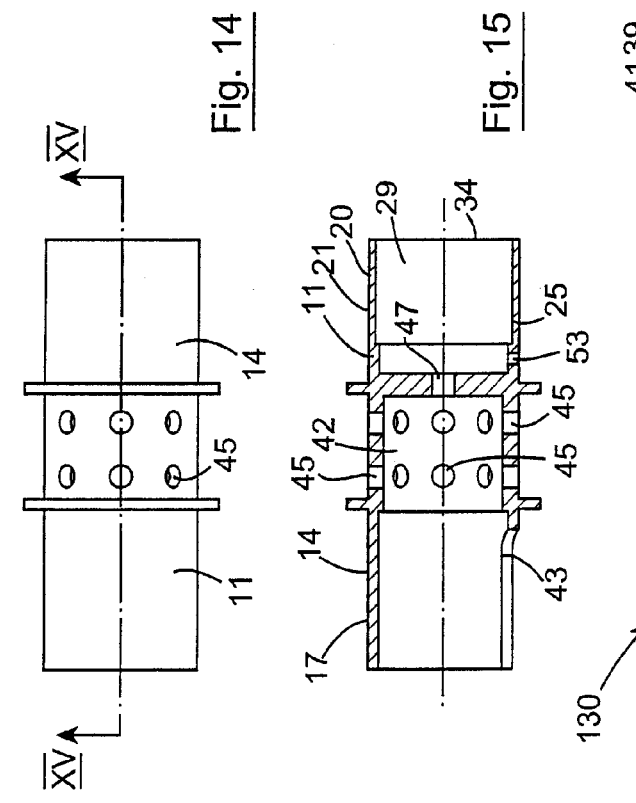
Fig. 14
Fig. 15
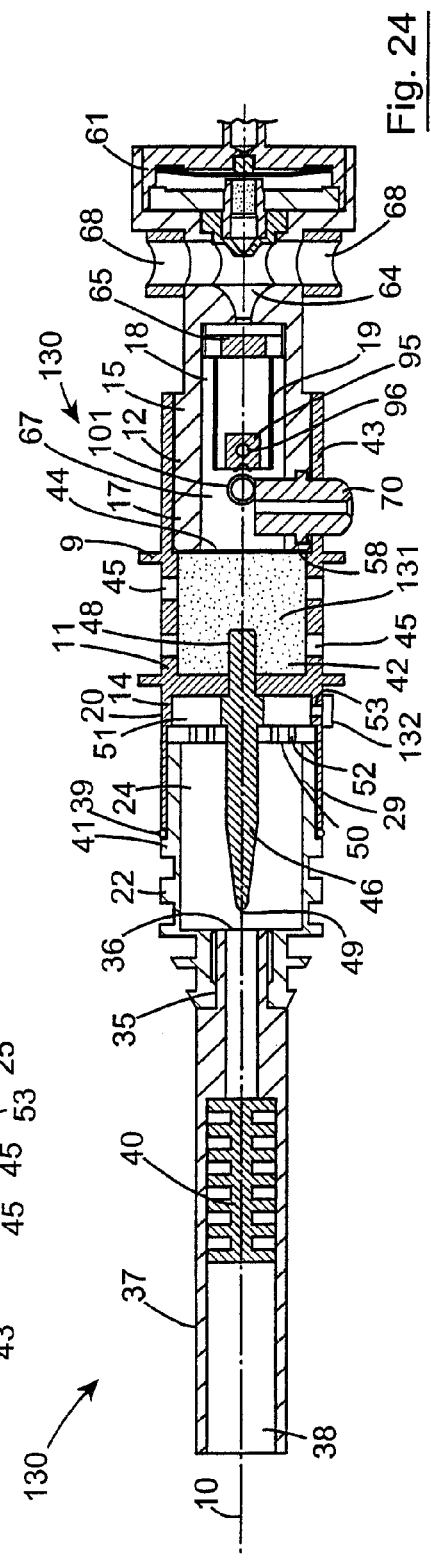
Fig. 24

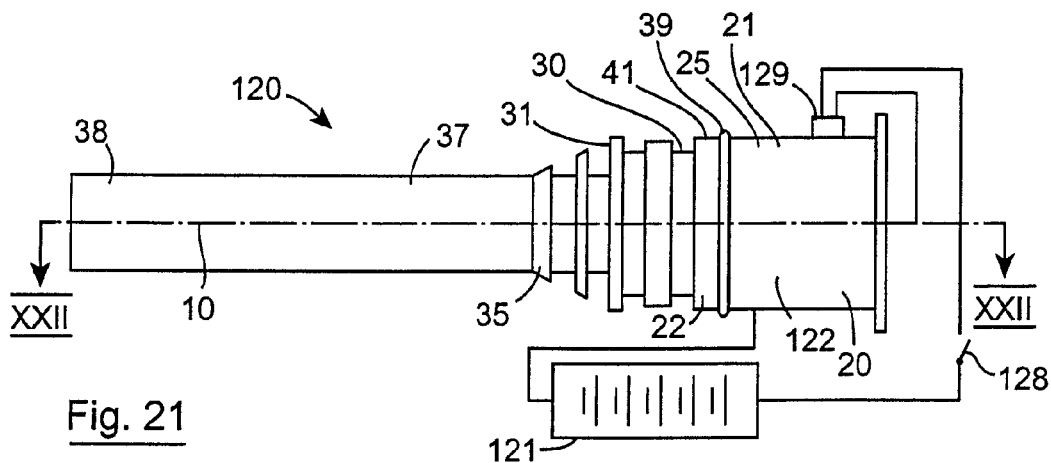
Fig. 21
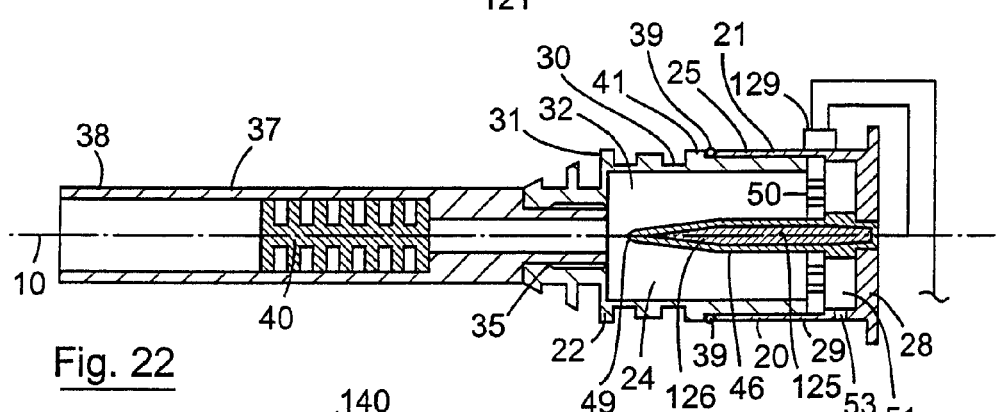
Fig. 22
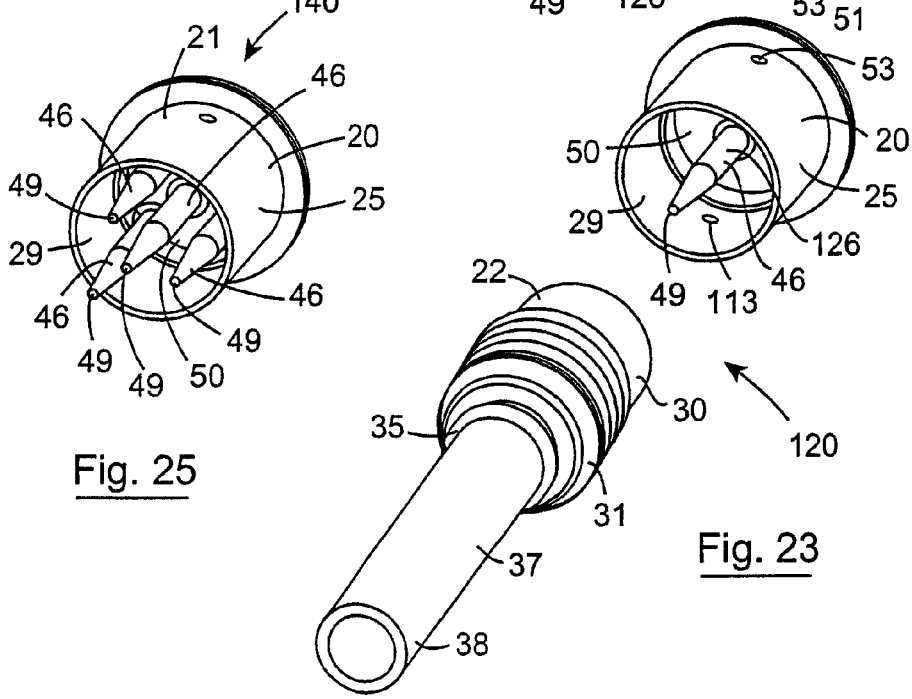
Fig. 25
Fig. 23

DEVICE FOR VAPORISING VAPORISABLE MATTER

The present invention relates to a device for vaporising vaporisable matter to produce an aerosol for inhaling. For example, the device is suitable for vaporising vaporisable matter which comprises one or more of flavour constituents, medicinal constituents and psychoactive constituents, such as tobacco, mullein, passion flower, cloves, yohimbe, mint, tea, eucalyptus, camomile and other such herbs and plant matter. The device is also suitable for use for vaporising medicinal compounds to form an aerosol for inhaling for rapid absorption into the bloodstream.

Herbs, for example, tobacco and the like are smoked by burning, in order to release psychoactive constituents, which are then inhaled. The psychoactive constituents are released into the fumes of combustion, which are then inhaled. However, the burning of such herbs, as well as producing psychoactive constituents also produces toxins, which largely result from the actual combustion process. Such toxins may be carcinogenic, and/or may result in lung and heart disease. Thus, the smoking of such herbs and other such plant matter is hazardous and undesirable, for example, it is now well established that smoking tobacco products, such as cigarettes can lead to lung and heart disease.

An alternative to releasing flavour, medicinal and psychoactive constituents from such herbs and plant matter by smoking is to raise the temperature of the herb or plant matter to an appropriate temperature for causing the vaporisable constituent or constituents of the herb or plant matter to be vaporised to produce an aerosol, and then inhale the aerosol. However, the temperature range at which such constituents in herbs and plant matter can be vaporised to form an aerosol ranges from approximately 125° C. to 400° C. If the temperature is below 125° C., in general, an aerosol of the constituent or constituents is not produced. However, if the temperature to which the herb or plant matter is heated exceeds 400° C., combustion of the herb or plant matter may commence, and additionally, undesirable constituents and toxins may be vaporised. Additionally, the desirable constituents of tobacco, in general, vaporise at temperatures in the range of 125° C. to 400° C., and in particular at temperatures in the range of 130° C. to 250° C., while the undesirable constituents may commence to vaporise at temperatures in excess of 250° C. In general, some undesirable constituents of tobacco tend to vaporise to produce an aerosol at temperatures above 250° C., and in general, undesirable constituents tend to be vaporised from tobacco at temperatures in excess of 400° C. Thus, it is desirable to maintain the tobacco at a temperature in the range of 130° C. to 250° C. in order to produce an aerosol of the desirable constituents, and to prevent an aerosol of the undesirable constituents of tobacco being produced. Thus, in order to satisfactorily produce an aerosol of flavour, medicinal and psychoactive constituents in herbs and plant matter, the temperature at which the herb or plant matter is maintained for producing the aerosol must be controlled within reasonably tight tolerances.

It is known to provide apparatus for vaporising constituents of herbs, such as tobacco to produce an aerosol. Such apparatus may be electrically powered or gas powered. Electrically powered apparatus, in general, comprise an electrically powered heating element for heating the tobacco or herb to a desired temperature in a vaporising chamber to produce the aerosol. A tube extending from the vaporising chamber accommodates the aerosol to a mouthpiece for facilitating inhaling of the vaporised constituents. Such an electrically powered device for vaporising constituents of tobacco is illustrated in U.S. Pat. No. 5,144,962 of Counts, et al assigned to Philip Morris Incorporated.

While such devices may be powered by a battery, in general, the power requirement for providing sufficient heat for maintaining the tobacco or herb at the appropriate temperature to produce an aerosol is relatively high, thus leading to relatively short battery life. In general, to overcome this problem, such devices are powered by mains electricity. However, a serious disadvantage of powering such devices with mains electricity is that they are effectively no longer portable, since one can only use the devices in the presence of a supply of mains electricity.

Gas powered devices for producing an aerosol from tobacco and other such herbs and plant matter tend to overcome the lack of portability problem of mains electrically powered devices, since in general a fuel gas supply can be stored in an associated reservoir under pressure in liquid form, and a reasonable life can be obtained from a charge of liquefied gas in a relatively small size reservoir. Such gas powered devices heat the tobacco or other herb by flame combustion or by catalytically converting the fuel gas to heat. However, in general, the temperature at which fuel gas is converted to heat either by flame combustion or catalytic conversion tends to be relatively high, and in the case of catalytic conversion, in general, catalytic combustion elements tend to operate at temperatures in the range of 600° C. to 900° C. and more commonly at temperatures in the range of 800° C. to 900° C. Thus, in general, in such gas powered devices the tobacco tends to be heated to temperatures considerably greater than the desired temperature range of 130° C. to 250° C., and commonly the tobacco may be heated at temperatures up to and in excess of 400° C. This is undesirable, since heating tobacco to such high temperatures can lead to combustion of the tobacco, and furthermore, at such high temperatures undesirable toxic constituents are also vaporised and become entrained in the aerosol. Examples of gas powered vaporising devices are disclosed in U.S. Pat. No. 5,944,025 of Cook, et al assigned to Brown & Williamson Tobacco Company and U.S. Pat. No. 6,089,857 of Matsuura, et al assigned to Japan Tobacco Inc. U.S. Pat. No. 5,944,025 discloses an elongated tubular member which comprises a vaporising chamber in which tobacco, constituents of which are to be vaporised to produce an aerosol, is located. Air is drawn through a reservoir containing an absorbent material impregnated with a liquid fuel for mixing vapour of the liquid fuel with the air. The fuel/air mixture is drawn through a catalyst coated ceramic tube where the fuel/air mixture is converted to heat by a catalytic reaction. Hot exhaust gases from the catalytic reaction are drawn into the vaporising chamber as one draws on the device, and the heated exhaust gases raise the temperature of the tobacco in the vaporising chamber to produce an aerosol, which is then drawn from the vaporising chamber and inhaled. However, a problem with this device is that the exhaust gases are mixed with the aerosol and inhaled by a user. This is clearly undesirable, since a user is subjected to the products of combustion resulting from the conversion of the fuel gas/air mixture to heat by the catalyst.

U.S. Pat. No. 6,089,857 discloses a device for heating tobacco to produce an aerosol for inhaling thereof which overcomes the problem of the mixing of the products of combustion with the aerosol of U.S. Pat. No. 5,944,025. The device of U.S. Pat. No. 6,089,857 comprises a fuel gas reservoir for storing fuel gas, and the fuel gas is burnt with flame combustion as it issues from a nozzle. A vaporising chamber for the tobacco or other herb is located in an exhaust duct through which exhaust gases from the flame combustion of the gas pass and heat the vaporising chamber in order to produce the aerosol. Air is drawn into the vaporising chamber as one draws on a mouthpiece extending from the vaporising chamber for drawing the aerosol from the vaporising chamber for inhaling thereof. While this device avoids mixing of exhaust gases of combustion with the aerosol, it suffers from the disadvantage that it is difficult, if not impossible, to regulate the temperature to which the tobacco is raised. Indeed, the device of U.S. Pat. No. 5,944,025 suffers from a similar disadvantage, as do other known gas powered vaporising devices, in that, in general, it is not possible to prevent the temperature of the tobacco rising to undesirably high temperatures.

Other devices for vaporising vaporisable constituents of tobacco to form an aerosol are of pipe-like construction, and the tobacco or herb to be heated is placed in a bowl of the pipe. Such a vaporising device is disclosed in U.S. Published Patent Application Specification No. 2004/0031495 of Steinberg. The vaporising device disclosed in this U.S. published Application specification comprises a pipe which is substantially similar to a smoking pipe in which the herb, typically, tobacco to be vaporised is located in a bowl portion of the pipe. A heat resistant and porous flame filter is located in the bowl above the herb, and a flame from a match or cigarette lighter is used to heat the porous filter while air is being drawn through the pipe. Thus, a mixture of air and the products of combustion from the flame are mixed in the porous filter and drawn through the herb in the bowl for heating the herb for in turn producing an aerosol of vaporisable constituents of the herb. The mixture of air, the products of combustion and the aerosol are then drawn through a mouthpiece of the pipe and inhaled. Due to the fact that the flame is played on the heat resistant porous flame filter, there is a danger of the flame being drawn through the filter and thus causing combustion of the herb in the bowl of the pipe. However, even where the herb does not combust, the products of combustion of the flame are inhaled along with the aerosol. This is undesirable.

There is therefore a need for a portable device for vaporising vaporisable matter from a herb or other plant matter to produce an inhaleable aerosol, in which the temperature of the vaporisable matter may be controlled more accurately than in devices known heretofore, and in which the products of combustion are segregated from the aerosol produced from the herb or plant matter so that only the aerosol and air is drawn from the device.

The present invention is directed towards providing such a device.

According to the invention there is provided a device for vaporising vaporisable matter, the device comprising a combustion chamber housing defining a combustion chamber, a gas catalytic combustion element located in the combustion chamber for converting fuel gas to heat for heating the combustion chamber housing, a vaporising chamber housing defining a vaporising chamber for the vaporisable matter, the vaporising chamber housing being in heat conducting relationship with the combustion chamber housing for transfer of heat thereto from the combustion chamber housing for heating the vaporisable matter in the vaporising chamber, wherein a temperature responsive control valve responsive to a temperature indicative of the temperature of the vaporising chamber is provided for controlling the supply of fuel gas to the combustion chamber to maintain the temperature within the vaporising chamber at a vaporization temperature of a vaporisable constituent of the vaporisable matter for producing an aerosol thereof.

In one embodiment of the invention the gas catalytic combustion element comprises a thermal mass for maintaining a portion of the gas catalytic combustion element at a temperature at or above the ignition temperature of the gas catalytic combustion element while fuel gas to the combustion chamber is isolated therefrom by the temperature responsive control valve. Preferably, the thermal mass is matched with and co-operates with the temperature responsive control valve for maintaining the portion of the gas catalytic combustion element at the temperature at or above the ignition temperature of the gas catalytic combustion element while fuel gas to the combustion chamber is isolated therefrom by the temperature responsive control valve. Advantageously, the thermal mass is formed separate of the gas catalytic combustion element and is in heat conducting engagement with the portion of the gas catalytic combustion element to be maintained at the temperature at or above the ignition temperature of the gas catalytic combustion element while fuel gas to the combustion chamber is isolated therefrom by the temperature responsive control valve.

In one embodiment of the invention the thermal mass is spaced apart from the combustion chamber housing for minimising heat transfer from the thermal mass to the combustion chamber housing. Preferably, the thermal mass is located within the gas catalytic combustion element. Advantageously, a tab shaped portion of the gas catalytic combustion element extends from the gas catalytic combustion element into a fuel gas passageway defined by the gas catalytic combustion element, and the thermal mass is located on and in heat conductive engagement with the tab portion. Preferably, the gas catalytic combustion element is of sleeve shape construction having a hollow core for forming the fuel gas passageway for accommodating fuel gas therethrough, and the tab portion of the gas catalytic combustion element extends into the hollow core.

In one embodiment of the invention the gas catalytic combustion element is operable at an operating temperature in the range of 600° C. to 900° C. for converting fuel gas to heat, and the thermal mass and the temperature responsive control valve co-operate for maintaining the temperature in the vaporising chamber at a temperature in the range of 100° C. to 500° C. Preferably, the thermal mass and the temperature responsive control valve co-operate for maintaining the temperature in the vaporising chamber at a temperature in the range of 125° C. to 400° C. Advantageously, the thermal mass and the temperature responsive control valve co-operate for maintaining the temperature in the vaporising chamber at a temperature in the range of 130° C. to 300° C. Ideally, the thermal mass and the temperature responsive control valve co-operate for maintaining the temperature in the vaporising chamber at a temperature in the range of 130° C. to 250° C.

In another embodiment of the invention a mouthpiece communicating with the vaporising chamber facilitates drawing of the aerosol from the vaporising chamber, and a heat sink means is located intermediate the vaporising chamber and the mouthpiece.

In a further embodiment of the invention the heat sink means acts as a condensing means for condensing undesirable vaporised constituents of the vaporisable matter drawn from the vaporising chamber. Preferably, the heat sink means comprises a heat sink member of heat conductive material located in an aerosol accommodating tube extending between the vaporising chamber and the mouthpiece. Advantageously, the heat sink member comprises an elongated core member of heat conductive material, and a plurality of spaced apart heat exchange fins extending from the core member. Ideally, the heat exchange fins extend transversely of the core member, and preferably, each heat exchange fin extends around the core member and is in sealable engagement with the aerosol accommodating tube, and adjacent pairs of heat exchange fins define with the core member and the aerosol accommodating tube respective galleries.

In one embodiment of the invention an opening is formed in each heat exchange fin for accommodating the aerosol from one gallery to the next adjacent gallery. Preferably, the heat exchange fins are located relative to each other so that the openings in adjacent heat exchange fins are spaced apart circumferentially from each other so that the galleries and the openings through the heat exchange fins define a tortuous passageway for the aerosol being drawn through the aerosol accommodating tube from one end of the heat sink means to the other end thereof. Advantageously, the opening through each heat exchange fin is located adjacent a peripheral edge thereof.

Preferably, the core member is a solid member, and advantageously, the heat exchange fins are of heat conductive material.

In one embodiment of the invention the heat exchange fins act as the condensing means.

In one embodiment of the invention the aerosol accommodating tube is of plastics material.

In another embodiment of the invention a heat transfer member of heat conductive material extends into the vaporising chamber for transferring heat into the vaporising chamber. Preferably, the heat transfer member tapers towards its distal end. Advantageously, the heat transfer member tapers to a sachet puncturing point adjacent its distal end for puncturing a sachet of the vaporisable matter.

In one embodiment of the invention a plurality of spaced apart elongated heat transfer members extend into the vaporising chamber. Preferably, the heat transfer members extend into the vaporising chamber parallel to each other.

In another embodiment of the invention an exhaust gas chamber is located between the vaporising chamber and the combustion chamber, the exhaust gas chamber communicating with the combustion chamber for receiving exhaust gases therefrom, and being isolated from the vaporising chamber by a heat exchange means for preventing exhaust gases entering the vaporising chamber from the exhaust gas chamber and for transferring heat from the exhaust gases to the vaporising chamber. Preferably, a heat conductive gauze type material is located in the exhaust gas chamber for facilitating the transfer of heat from exhaust gases in the exhaust gas chamber to the heat exchange means. Advantageously, the heat conductive gauze type material is a knitted metal fabric randomly folded to substantially fill the exhaust gas chamber.

Preferably, the heat exchange means is formed by a primary partition wall of heat conductive material located between the vaporising chamber and the exhaust gas chamber, and each heat transfer member extends from the primary partition wall into the vaporising chamber. Advantageously, each heat transfer member extends from the primary partition wall into the exhaust gas chamber for facilitating heat exchange between the exhaust gases and the heat transfer member.

In one embodiment of the invention a secondary partition wall of perforated material extends transversely in the vaporising chamber parallel to and spaced apart from the primary partition wall and forms with the primary partition wall and a portion of the vaporising chamber housing an air inlet chamber, the vaporising chamber communicating with the air inlet chamber through the secondary partition wall for accommodating air into the vaporising chamber as the aerosol is drawn therefrom.

In another embodiment of the invention a primary air inlet is provided to the air inlet chamber for accommodating air into the air inlet chamber.

In a further embodiment of the invention a valving means is provided for facilitating selective closing the primary air inlet. Preferably, the valving means comprises a non-return valve for facilitating air through the primary air inlet to the air inlet chamber, and for preventing return flow through the primary air inlet from the air inlet chamber.

In another embodiment of the invention a secondary air inlet is provided downstream of the primary air inlet for accommodating air to the vaporising chamber. Preferably, the secondary air inlet is provided by an orifice, and an adjusting means for adjusting the area of the orifice is provided for altering the rate at which air is drawn through the secondary air inlet.

In another embodiment of the invention an exhaust gas port is provided from the exhaust gas chamber for accommodating exhaust gases therefrom.

Preferably, the combustion chamber housing and a portion of the vaporising chamber housing are formed from a main housing of heat conductive material. Advantageously, the vaporising chamber housing comprises a socket portion and a hollow plug portion, the hollow plug portion being releasably engageable with the socket portion for defining the vaporising chamber. Preferably, the socket portion is formed by the primary partition wall and a primary side wall extending around the primary partition wall defining with the primary partition wall a primary hollow interior region to form the socket portion, and the plug portion comprises an end cap and a secondary side wall extending around the end cap and defining therewith a secondary hollow interior region, the respective primary and secondary side walls forming respective open mouths to the respective primary and secondary hollow interior regions for facilitating communicating therebetween for forming the vaporising chamber.

In one embodiment of the invention the secondary side wall of the plug portion is releasably engageable within the primary side wall of the socket portion. Preferably, the socket portion of the vaporising chamber is formed by the main housing.

In one embodiment of the invention the main housing defines a longitudinally extending main central axis, the combustion chamber and the vaporising chamber being axially aligned with each other. Preferably, the combustion chamber and the vaporising chamber define respective central axes, the central axes thereof coinciding with the main central axis of the main housing. Advantageously, the exhaust gas chamber defines a central axis which coincides with the main central axis of the main housing. Preferably, an aerosol outlet port is provided from the vaporising chamber for accommodating aerosol therefrom, the aerosol outlet port defining a central axis which coincides with the main central axis of the main housing. Advantageously, the catalytic combustion element defines a main central axis which coincides with the main central axis of the main housing.

In one embodiment of the invention the temperature responsive control valve defines a central axis which coincides with the main central axis of the main housing. Preferably, a temperature responsive safety isolation valve is provided for isolating the combustion chamber from fuel gas in the event of the temperature of the combustion chamber housing exceeding a predetermined safe maximum temperature. Advantageously, the temperature responsive safety isolating valve is located upstream of the temperature responsive control valve, and defines a central axis which coincides with the main central axis of the main housing.

In another embodiment of the invention a mixing means is located intermediate the temperature responsive control valve and the combustion chamber for mixing fuel gas from the temperature responsive control valve with air for delivering a fuel gas/air mixture to the combustion chamber. Preferably, the mixing means defines a central axis, the central axis thereof coinciding with the main central axis of the main housing.

In one embodiment of the invention the temperature responsive control valve comprises a heat conductive valve housing defining a valve chamber, the heat conductive valve housing being in heat conducting relationship with the vaporising chamber housing, a bi-metal valving member located in the valve chamber and co-operating with one of a valve inlet and a valve outlet to the valve chamber for controlling the flow of fuel gas through the valve chamber in response to the temperature of the vaporising chamber housing. Preferably, the bi-metal valving member is of the type which transitions from one state to another, which are mirror images of each other, as the temperature of the bi-metal valving member transitions across a predetermined transition temperature, and the bi-metal valving member is constrained within the valve chamber to prevent transitioning of the bi-metal valving member between the respective states, so that the control of the flow of fuel gas through the temperature responsive control valve is analogue.

In another embodiment of the invention a fuel gas reservoir is provided for storing fuel gas in liquid form.

In one embodiment of the invention the device is adapted for vaporising vaporisable constituents in tobacco.

In another embodiment of the invention the temperature of the vaporising chamber is maintained at the minimum temperature for forming the aerosol from desirable vaporisable constituents of tobacco in order to minimise vaporising of tar and other undesirable constituents of the tobacco.

In a further embodiment of the invention the gas catalytic combustion element is located in the combustion chamber for defining with the combustion chamber a flame cavity for facilitating initial ignition of fuel gas in the flame cavity in a flame for raising the temperature of the gas catalytic combustion element to its ignition temperature. Preferably, an ignition means is provided to the flame cavity for igniting the fuel gas to burn in a flame in the flame cavity.

The invention also provides a device for vaporising vaporisable matter, the device comprising a vaporising chamber housing defining a vaporising chamber for the vaporisable matter, and a heating means, wherein a heat transfer means extends into the vaporising chamber for transferring heat from the heating means into the vaporising chamber to maintain the temperature within the vaporising chamber at a vaporization temperature of a vaporisable constituent of the vaporisable matter for producing an aerosol thereof.

In one embodiment of the invention there is provided the heat transfer means comprises an elongated heat transfer member.

The invention also provides a device for vaporizing vaporisable matter, the device comprising a vaporising chamber housing defining a vaporising chamber for the vaporisable matter, a heating means for heating the vaporising chamber housing for heating the vaporisable matter for producing an aerosol thereof, wherein a mouthpiece communicates with the vaporising chamber for facilitating drawing of the aerosol therefrom, and a heat sink means is located intermediate the vaporising chamber and the mouthpiece for cooling the aerosol.

In another embodiment of the invention the heat sink means forms a condensing means for condensing undesirable vaporised constituents of the vaporisable matter drawn from the vaporising chamber.

The advantages of the invention are many. In particular, the temperature to which the vaporisable matter is heated is relatively accurately controllable, and in general, can be controlled accurately to within ±5° C. of a temperature within a temperature range of 130° C. to 250° C. This is achieved by virtue of the fact that fuel gas is supplied to the combustion chamber through the temperature responsive control valve which is responsive to a temperature indicative of the temperature within the vaporising chamber.

A particularly important advantage of the invention is achieved by the provision of the thermal mass in heat conductive engagement with a portion of the gas catalytic combustion element. The provision of the thermal mass permits the device to operate at temperatures within the vaporising chamber significantly lower than the normal operating temperature of the gas catalytic combustion element. With operating temperatures of the gas catalytic combustion element in the range of 800° C. to 900° C., the provision of the thermal mass in heat conductive engagement with a portion of the gas catalytic combustion element permits the device to operate at temperatures in the vaporising chamber within a range from 130° C. to 250° C. In order to operate the device at a temperature within the vaporising chamber within the range of 130° C. to 250° C., the temperature responsive control valve must operate to periodically isolate the gas catalytic combustion element from the fuel gas supply for relatively lengthy periods. Without the thermal mass, this would result in the gas catalytic combustion element falling below its ignition temperature, and thus, automatic re-ignition of the gas catalytic combustion element on subsequent reinstatement of the fuel gas by the temperature responsive control valve would not occur. However, by providing the thermal mass, the portion of the gas catalytic combustion element in heat conducting engagement with the thermal mass is maintained at or above the ignition temperature of the gas catalytic combustion element during periods of isolation of the gas catalytic combustion element from the fuel gas, and thus on subsequent reinstatement of the fuel gas to the gas catalytic combustion element, the portion of the gas catalytic combustion element which has been maintained at or above the ignition temperature of the gas catalytic combustion element immediately commences to convert the fuel gas to heat, thus progressively and rapidly raising the remainder of the gas catalytic combustion element to its ignition temperature for full conversion of the fuel gas to heat by the gas catalytic combustion element. This advantage is achieved by sizing the thermal mass to co-operate with the temperature responsive control valve, so that the portion of the gas catalytic combustion element adjacent the thermal mass is maintained at or above the ignition temperature of the gas catalytic combustion element for the maximum duration of isolation of the gas catalytic combustion element from the fuel gas by the temperature responsive control valve.

A further advantage of the invention is that the heating of the vaporisable material is carried out relatively efficiently. This is achieved by virtue of the fact that heat is transferred from the combustion chamber housing to the vaporising chamber housing by heat conduction, and where the combustion chamber housing and a portion of the vaporising chamber housing are formed from the main body member, which is of heat conductive material, the heat transfer efficiency by conduction is relatively efficient from the combustion chamber housing to the vaporising chamber housing. Additionally, the provision of one or more heat transfer members extending into the vaporising chamber further enhances heat transfer from the combustion chamber housing into the vaporising chamber. Indeed, the provision of the exhaust gas chamber located between the combustion chamber and the vaporising chamber further adds to the efficiency of heat transfer from the combustion chamber to the vaporising chamber, since heat is transferred from the exhaust gases through the heat exchange means into the vaporising chamber. Additionally, by extending each heat transfer member into the exhaust gas chamber, further efficiency in heat transfer is achieved, since the heat transfer members further assist in transferring heat from the exhaust gases into the vaporising chamber.

A further advantage of the invention is achieved when a heat conductive gauze type material is located in the exhaust gas chamber, and in particular, when the heat conductive gauze type material substantially fills the exhaust gas chamber. The heat conductive gauze type material tends to diffuse the exhaust gas in the exhaust gas chamber, and slows down the passage of the exhaust gas through the exhaust gas chamber. Since the gauze type material is heat conductive, heat is extracted from the exhaust gases by the gauze type material, which in turn transfers the heat from the exhaust gases into the heat exchange means for transfer into the vaporising chamber. The provision of the heat conductive gauze type material in the form of a knitted metal fabric is a particularly advantageous form of the gauze type material, and thus further enhances heat transfer from the exhaust gases in the exhaust gas chamber.

By forming the combustion chamber, the exhaust gas chamber and the vaporising chamber in the main body member, heat transfer from the combustion chamber to the vaporising chamber is further enhanced, in that direct heat transfer by heat conduction is achieved from the combustion chamber housing to the vaporising chamber housing, and in turn into the vaporising chamber.

An important advantage of the invention is achieved when the heat sink means is provided. The heat sink means has two advantages, firstly, it cools the aerosol being drawn from the vaporising chamber, thus avoiding any danger of the mouth of a user being burnt, and in particular, it cools the vapours drawn initially from the vaporising chamber after the vaporisable matter in the vaporising chamber has been brought up to heat. In general, vaporisable matter, although pre-dried, tends to contain moisture. Initially the moisture is driven off as water vapour or steam. This steam typically is at a relatively high temperature and if drawn directly into the mouth of a user would burn the mouth and tongue of a user. The heat sink means cools and condenses the steam, thereby avoiding burning of a user.

An additional and important advantage of the heat sink means is that it also acts as a condensing means for condensing less desirable vaporised constituents in the aerosol as the aerosol is being drawn across the heat exchange means. While the device may be operated at sufficiently low temperatures to produce an aerosol of desirable vaporisable constituents of tobacco, and which minimise the production of aerosols of tarry and other toxic constituents, in general, it is impossible to avoid some tarry and other toxic constituents being vaporised, and thus entrained in the aerosol. The provision of the heat sink means when it is adapted to act as a condensing means tends to cause tarry and other toxic constituents to condense on the heat sink means. Such condensed constituents may be readily removed from the heat sink means by periodically removing the heat sink means from the device for cleaning.

A further advantage of the invention is achieved when the gas catalytic combustion element is located in the combustion chamber to define with the combustion chamber a flame cavity which facilitates fuel gas to be initially burnt in a flame for raising the temperature of the gas catalytic combustion element to its ignition temperature. By providing the ignition means for igniting the fuel gas to burn in a flame in the flame cavity, the device can readily easily be operated by merely supplying fuel gas to the combustion chamber and operating the ignition means to ignite the fuel gas to burn in a flame in the flame cavity. Once the flame has raised an adjacent portion of the gas catalytic combustion element to its ignition temperature, the portion of the gas catalytic combustion element which has been raised to its ignition temperature commences to convert the fuel gas to heat by catalytic action, which progressively and rapidly raises the remainder of the gas catalytic combustion element to its ignition temperature for converting the fuel gas to heat. This starves the flame of fuel gas, which is rapidly extinguished, thereby permitting heating of the device exclusively by catalytic conversion of the fuel gas to heat.

Figure 4:
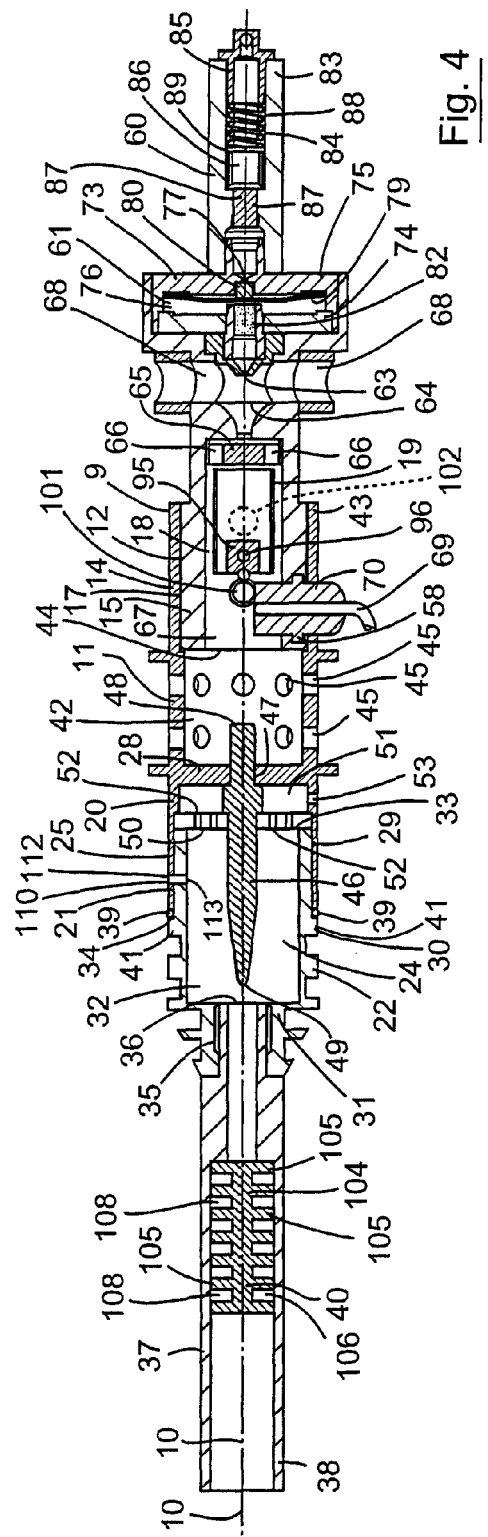
Figure 17:
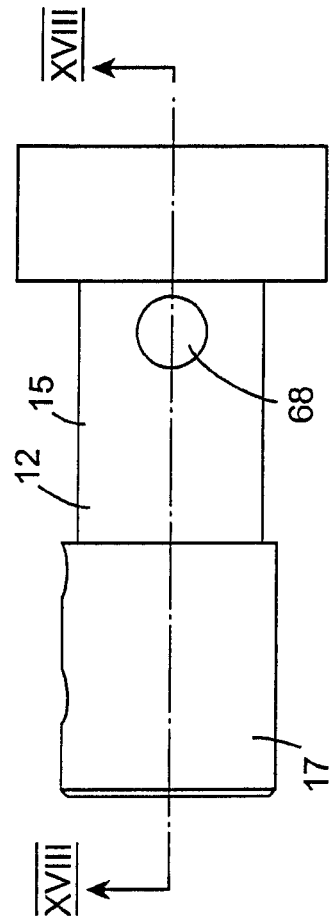
Figure 18:
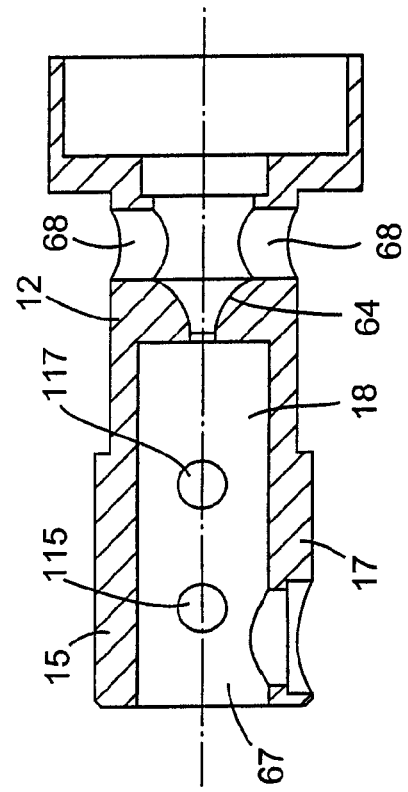
Figure 16:
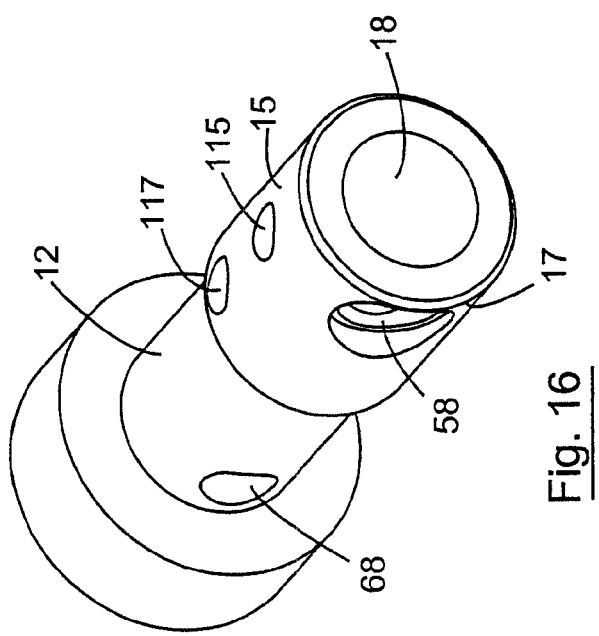
Figure 19:
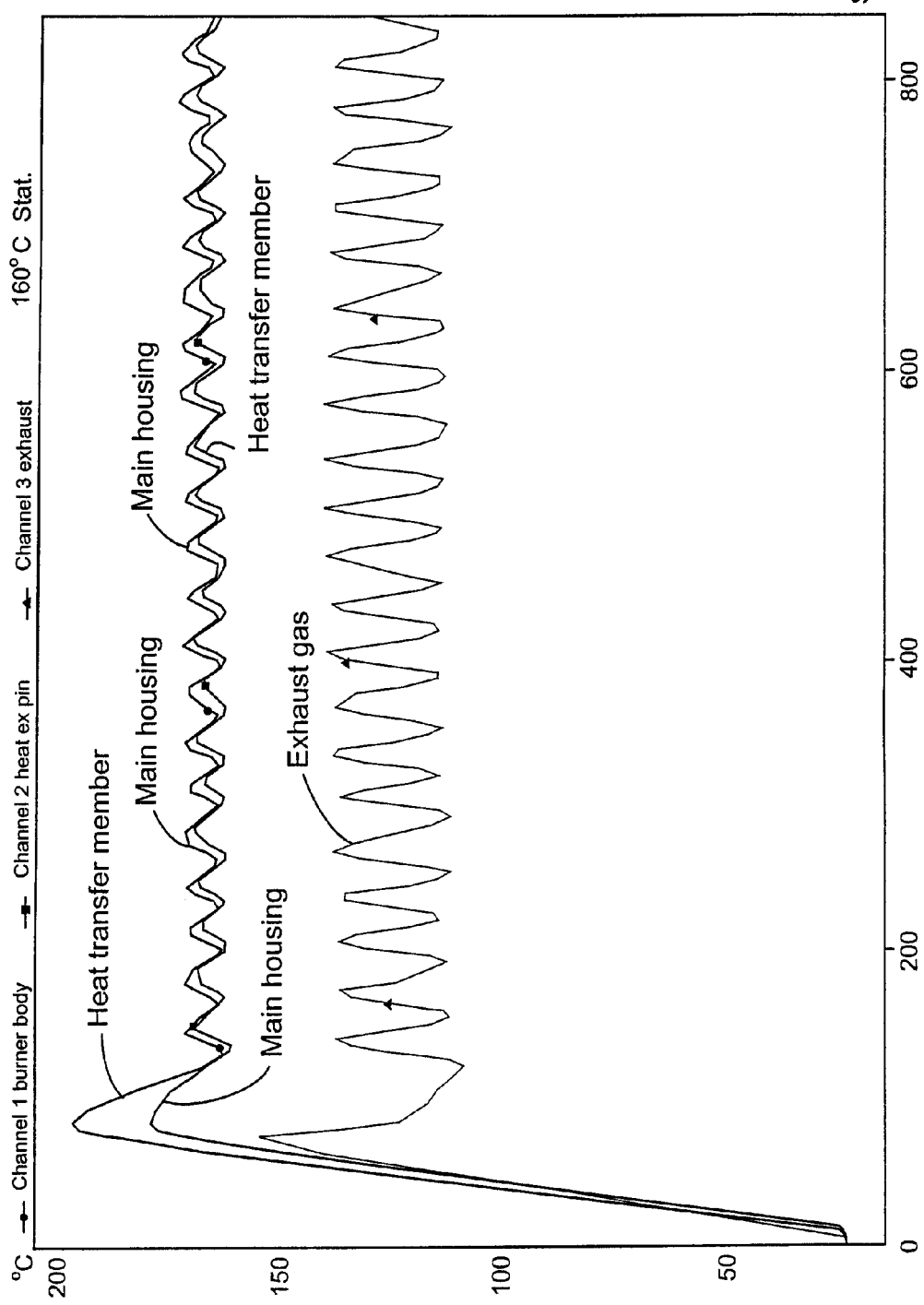
Figure 20:
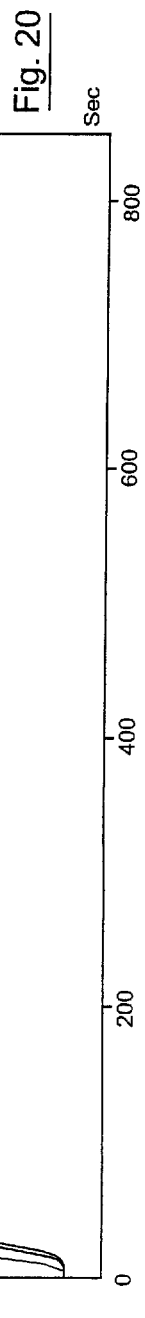

The invention and its many advantages will become more readily apparent from the following description of some preferred embodiments thereof, which are given by way of example only, with reference to the accompanying drawings, in which:

FIG. 1 is a perspective view of a device according to the invention for vaporising vaporisable matter to produce an aerosol thereof, FIG. 2 is a front elevational view of the device of FIG. 1 with a portion of the device removed, FIG. 3 is an enlarged front elevational view of a portion of the device of FIG. 1, FIG. 4 is a transverse cross-sectional underneath plan view of the portion of FIG. 3 on the line IV-IV of FIG. 3, FIG. 5 is a perspective view of a detail of the device of FIG. 1, FIG. 6 is a perspective view of another detail of the device of FIG. 1, FIG. 7 is a transverse cross-sectional top plan view of a portion of the device of FIG. 1 on the line VII-VII of FIG. 3, FIG. 8 is a perspective view of another detail of the device of FIG. 1, FIG. 9 is an end elevational view of the detail of FIG. 8 of the device of FIG. 1, FIG. 10 is a transverse cross-sectional front elevational view of another detail of the device of FIG. 1, FIG. 11 is an end view of the detail of FIG. 10 of the device of FIG. 1, FIG. 12 is an end view of another detail of the device of FIG. 1, FIG. 13 is a perspective view of a portion of the device of FIG. 1, FIG. 14 is an elevational view of the portion of FIG. 13 of the device of FIG. 1, FIG. 15 is a transverse cross-sectional underneath plan view of the portion of FIG. 14 on the line XV-XV of FIG. 14, FIG. 16 is a perspective view of another portion of the device of FIG. 1, FIG. 17 is an elevational view of the portion of FIG. 16 of the device of FIG. 1, FIG. 18 is a transverse cross-sectional underneath plan view of the portion of FIG. 17 on the line XVIII-XVIII of FIG. 17, FIG. 19 illustrates waveforms representative of measured temperatures of the device of FIG. 1 operating under one condition, FIG. 20 illustrates waveforms representative of measured temperatures of the device of FIG. 1 operating under a different condition to that of FIG. 19, FIG. 21 is a front elevational view of a portion of a device according to another embodiment of the invention for vaporising vaporisable matter to produce an aerosol thereof, FIG. 22 is a transverse cross-sectional plan view of the portion of the device of FIG. 21 on the line XXII-XXII of FIG. 21, FIG. 23 is an exploded perspective view of the device of FIG. 21, FIG. 24 is a view similar to FIG. 4 of a portion of a device according to another embodiment of the invention for vaporising vaporisable matter to produce an aerosol thereof, and FIG. 25 is a perspective view of a detail of a device according to a further embodiment of the invention for vaporising vaporisable matter to produce an aerosol thereof.

Referring to the drawings and initially to FIGS. 1 to 20, there is illustrated a device according to the invention, indicated generally by the reference numeral 1, for vaporising vaporisable matter, in this case tobacco, to produce an inhaleable aerosol from vaporisable constituents of the tobacco. The device 1 is encased in a two-part casing 3 formed by first and second casing shells 4 and 5 of injection moulded plastics material, which are secured together by screws (not shown). An elongated main housing 9 of circular transverse cross-section is located within the casing 3 and defines a longitudinally extending main central axis 10. The main housing 9 is of heat conductive material, which in this embodiment of the invention is of aluminium, and comprises two parts, namely, an outer part 11 and an inner part 12. The outer part 11 of the main housing 9 forms a cylindrical outer side wall 14, while the inner part 12 of the main housing 9 forms a cylindrical inner side wall 15. The inner and outer side walls 15 and 14 of the main housing 9 form a combustion chamber housing 17 within which a combustion chamber 18 is formed. A heating means, in this embodiment of the invention a gas catalytic combustion element 19, which is described in more detail below, is located within the combustion chamber 18 for converting fuel gas to heat for heating the combustion chamber housing 17 and in turn the main housing 9.

The outer part 11 of the main housing 9 also forms a cylindrical socket portion 20 of a vaporising chamber housing 21 which co-operates with a releasable plug portion 22 of the vaporising chamber housing 21 to form a vaporising chamber 24 within which the tobacco is located for vaporising the vaporisable constituents thereof to produce the aerosol. The plug portion 22 is also of a heat conductive material, which is also aluminium. The outer side wall 14 of the outer part 11 of the main housing 9 forms a primary side wall 25 of the socket portion 20, which with a primary partition wall 28 extending transversely of the outer side wall 14 forms a primary hollow interior region 29 of the socket portion 20 within which the plug portion 22 of the vaporising chamber housing 21 is releasably engageable. The plug portion 22 comprises a cylindrical secondary side wall 30 and an end cap 31 extending transversely of the secondary side wall 30, which with the secondary side wall 30 defines a secondary hollow interior region 32 within which the tobacco is placed. The secondary side wall 30 defines an open mouth 33 to the secondary hollow interior region 32, while the primary side wall 25 of the socket portion 20 defines an open mouth 34 to the primary hollow interior region 29 for receiving the plug portion 22, so that when the plug portion 22 is engaged in the primary hollow interior region 29, the secondary hollow interior region 32 communicates with the primary hollow interior region 29 through the open mouth 33 to form with the primary hollow interior region 29 the vaporising chamber 24. A sealing means comprising an O-ring seal 39 extends around the secondary side wall 30 adjacent an annular shoulder 41 for abutting the primary side wall 25 adjacent the open mouth 34 to the primary hollow interior region 29 for sealing the vaporising chamber 24, when the plug portion 22 is fully engaged in the socket portion 20.

An aerosol accommodating outlet port 35 in the end cap 31 accommodates the aerosol from the vaporising chamber 24. A downstream disc 36 of metal mesh material located in the secondary hollow interior region 32 of the plug portion 22 adjacent the aerosol accommodating outlet port 35 retains the tobacco in the vaporising chamber 24. An aerosol accommodating tube 37 of plastics material extending from the aerosol accommodating outlet port 35 terminates in a mouthpiece 38 for facilitating inhaling of the aerosol from the vaporising chamber 24.

A heat sink means comprising a heat sink member 40 of heat conductive material, namely, aluminium is located in the aerosol accommodating tube 37 for cooling the aerosol as it is drawn through the aerosol accommodating tube 37, and for condensing tarry and other toxic vaporised constituents of the tobacco in the aerosol being drawn through the aerosol accommodating tube 37, as will be described in more detail below.

An exhaust gas chamber 42 is formed in the main housing 9 by the outer side wall 14 of the outer part 11 of the main housing 9 between the combustion chamber 18 and the vaporising chamber 24. The exhaust gas chamber 42 communicates with the combustion chamber 18 through a metal gauze membrane 44 which extends transversely of the outer side wall 14 at the downstream end of the combustion chamber 18. A plurality of exhaust gas ports 45 extending through the outer side wall 14 which forms the exhaust gas chamber 42 accommodate exhaust gases from the exhaust gas chamber 42. The primary partition wall 28 forms a heat exchange means for facilitating the transfer of heat from the exhaust gases in the exhaust gas chamber 42 into the vaporising chamber 24, and also for preventing entry of exhaust gases from the exhaust gas chamber 42 into the vaporising chamber 24.

A heat transfer means, namely, an elongated heat transfer member 46 sealably secured in a bore 47 through the primary partition wall 28 extends into the vaporising chamber 24 for transferring heat into tobacco in the vaporising chamber 24. The heat transfer member 46 is of heat conductive material, namely, aluminium, and extends at 48 into the exhaust gas chamber 42 for facilitating efficient transfer of heat from the exhaust gases in the exhaust gas chamber 42 into the vaporising chamber 24. The heat transfer member 46 tapers towards its distal end and terminates in a point 49 for puncturing a sachet of tobacco if the tobacco is placed in a sachet in the secondary hollow interior region 32 of the plug portion 22, as the plug portion 22 is being engaged in the socket portion 20.

A secondary partition wall 50 extends transversely across the primary hollow interior region 29 parallel to and spaced apart from the primary partition wall 28 for defining with the primary partition wall 28 and the primary side wall 25 an air inlet chamber 51. The secondary partition wall 50 is of perforated aluminium with a plurality of air accommodating holes 52 extending therethrough for accommodating air from the air inlet chamber 51 to the vaporising chamber 24 as the aerosol is being drawn from the vaporising chamber 24. A primary air inlet port 53 accommodates air into the air inlet chamber 51 to be drawn into the vaporising chamber 24.

A rechargeable fuel gas reservoir 55 located in the casing 3 stores fuel gas in liquid form, which in this embodiment of the invention is a butane based gas in liquid form. Fuel gas is delivered from the fuel gas reservoir 55 through a pressure regulator 56 located in an outlet 57 from the reservoir 55 for adjusting the pressure of the fuel gas as it exits the fuel gas reservoir 55. A button operated on/off valve 62 also adjacent the outlet 57 from the reservoir 55 switches on and off the fuel gas from the fuel gas reservoir 55. A fuel gas pipe 59 couples the on/off valve 62 to a temperature responsive safety isolating valve 60, which is provided for isolating the fuel gas supply from the fuel gas reservoir 55 to the combustion chamber 18 in the event of the temperature of the main housing 9 exceeding a predetermined upper maximum safe working temperature. The temperature responsive safety isolating valve 60 is described in detail below.

A temperature responsive control valve 61, which is described below, is located downstream of the safety isolating valve 60 for controlling the supply of fuel gas to the combustion chamber 18 for maintaining the temperature within the vaporising chamber 24 at a predetermined temperature, which in this embodiment of the invention is in the range of 130° C. to 250° C. for vaporising desirable vaporisable constituents from the tobacco to produce the aerosol, and for minimising vaporization of undesirable constituents from the tobacco. An outlet nozzle 63 from the temperature responsive control valve 61 delivers fuel gas from the control valve 61 into a mixing means, namely, a venturi mixer 64 where the fuel gas is mixed with air. The venturi mixer 64 is formed in the inner part 12 of the main housing 9, and air ports 68 in the inner part of the main housing 9 accommodate air into the venturi mixer 64. A diffuser comprising a diffuser plate 65 having a plurality of bores 66 extending therethrough located intermediate the venturi mixer 64 and the combustion chamber 18 distributes fuel gas/air mixture from the venturi mixer 64 into the combustion chamber 18, and in turn to the gas catalytic combustion element 19, see FIG. 12.

The gas catalytic combustion element 19 is located in the combustion chamber 18 to define with the combustion chamber 18 a flame cavity 67 within which the fuel gas/air mixture is initially burnt in a flame for raising the temperature of the gas catalytic combustion element 19 to its ignition temperature, so that as the gas catalytic combustion element 19 reaches its ignition temperature it commences to convert fuel gas to heat, thus starving the flame of fuel gas/air mixture, which is then extinguished.

An electrode 69 extends through an electrically insulating mounting 70 into the flame cavity 67 and co-operates with the inner side wall 15 of the inner part 12 of the main housing 9 for causing a spark to arc between the electrode 69 and the inner side wall 15 for igniting the fuel gas initially to burn in a flame. The insulating mounting 70 is located in a bore 58 through the inner part 12 of the main housing 9, and a slot 43 in the outer part 11 of the main housing 9 accommodates the insulating mounting 70 therethrough. A piezo-electric ignition mechanism 71 located within the casing 3 is coupled to the electrode 69 for producing a voltage to cause the spark to arc between the electrode 69 and the inner side wall 15 of the main housing 9. A plunger 72 of the piezo-electric ignition mechanism 71 extends through the casing 3 for facilitating activation of the piezo-electric ignition mechanism 71 for causing the spark to arc between the electrode 69 and the inner side wall 15 of the main housing 9. The main housing 9 is earthed through an earth strap (not shown) to the piezo-electric ignition mechanism 71.

Turning now to the temperature responsive control valve 61, and referring in particular to FIG. 7, the temperature responsive control valve 61 is substantially similar to the temperature responsive control valve disclosed in PCT Published Application Specification No. WO 02/48591 of the present Applicant, and the disclosure thereof is incorporated herein by reference. The temperature responsive control valve 61 comprises a two-part valve housing 73 formed by an outer part 74 and an inner part 75 in sealable engagement with the outer part 74, and forming with the outer part 74 a valve chamber 76. The outer and inner parts 74 and 75 of the valve housing 73 are of heat conductive material, namely aluminium, and are in heat conducting engagement with the inner part 12 of the main housing 9. A valve inlet 77 in the outer part 74 of the valve housing 73 accommodates fuel gas from the safety isolating valve 60 into the valve chamber 76 and defines a valve seat 78. A bi-metal valving disc 79 is located in the valve chamber 76 and carries a valving element 80 which is engageable with the valve seat 78 for controlling the flow of fuel gas into the valve chamber 76. An outlet nozzle 81 located in the inner part 75 delivers fuel gas from the valve chamber 76 into the venturi mixer 64. The bi-metal valving disc 79 is a temperature responsive bi-metal disc of the type, which on being subjected to a predetermined temperature as the temperature is rising transitions from a first dished configuration to a second dished configuration which is a mirror image of the first dished configuration, and on being subjected to the same or a slightly lower predetermined temperature as the temperature is falling, transitions from the second configuration to the first configuration. However, in order to control the flow of fuel gas into the valve chamber 76 with an analogue type controlling action, the bi-metal valving disc 79 is constrained by a shoulder 107 of the inner part 75 of the valve housing 73 within the valve chamber 76 to prevent transitioning of the valving disc 79 between the first and second configurations. The operation of this type of temperature responsive control valve is described in PCT Published Application Specification No. WO 02/48591. A filter 82 located in the inner part 75 of the valve housing 73 between the outlet nozzle 81 and an outlet port 103 from the valve chamber 76 filters the fuel gas delivered to the outlet nozzle 81. As discussed above, the inner part 75 and the outer part 74 of the valve housing 73 are in heat conducting engagement with the inner part 12 of the main housing 9, and accordingly the valve housing 73 and in turn the valve chamber 76 and the bi-metal valving disc 79 are maintained at a temperature which is indicative of the temperature of the main housing 9, and since the vaporising chamber housing 21 is formed by part of the main housing 9, the temperature of the valve housing 73 and the bi-metal valving disc 79 is indicative of the temperature of the vaporising chamber housing 21 and in turn the temperature within the vaporising chamber 24. Thus, the bi-metal valving disc 79 is responsive to the temperature within the vaporising chamber 24. The thermal mass of the main housing 9, the plug portion 22 of the vaporising chamber housing 21 as well as the valve housing 73 and a body member 83 of the temperature responsive safety isolating valve 60 are thermally balanced so that the temperature responsive control valve 61 operates to control the supply of fuel gas to the combustion chamber 18 to maintain the temperature within the vaporising chamber 24 within the temperature range of 130° C. to 250° C. The temperature at which the main housing 9 is maintained by the temperature responsive control valve 61 is described below with reference to FIGS. 19 and 20.

The temperature responsive safety isolating valve 60 is substantially similar to a safety cut-out mechanism disclosed in PCT Published Application Specification No. WO 02/48591 and the disclosure therein is incorporated herein by reference. The body member 83 of the temperature responsive safety isolating valve 60 is of heat conducting material, namely, aluminium, and extends from and is in heat conducting engagement with the outer part 74 of the valve housing 73 of the temperature responsive control valve 61. A bore 84 extending through the body member 83 communicates with the valve inlet 77 of the temperature responsive control valve 61. An inlet port 85 is coupled to the fuel gas pipe 59 and delivers fuel gas from the fuel gas reservoir 55 into the bore 84. A slug 86 of plastics material impregnated with fibre glass material is located in the bore 84 and is a loose fit therein for permitting the flow of fuel gas through the bore 84 past the slug 86 from the inlet port 85 to the valve inlet 77 of the temperature responsive control valve 61. A porous sintered bronze filter 87 is located in the bore 84 downstream of the slug 86 for filtering and accommodating fuel gas therethrough. A compression spring 88 acting between the inlet port 85 and a perforated disc 89 urges the slug 86 towards the filter 87. The disc 89 is perforated for accommodating fuel gas therethrough. Longitudinal channels 90 and radial channels 91 extending in the slug 86 accommodate fuel gas past the slug 86 to the filter 87 and in turn to the valve inlet 77 of the temperature responsive control valve 61. The melt temperature of the plastics material of the slug 86 is such that when the temperature of the main housing 9 reaches a predetermined unsafe working temperature, the plastics material of the slug 86 melts, and the action of the compression spring 88 against the disc 89 urges the melting plastics material towards and into the sintered filter 87, thereby blocking the sintered filter 87 and preventing flow of fuel gas therethrough, thus isolating the temperature responsive control valve 61 and in turn the combustion chamber 18 from the fuel gas reservoir 55.

Turning now to the gas catalytic combustion element 19 and referring in particular to FIGS. 8 and 9, in this embodiment of the invention the gas catalytic combustion element comprises a perforated sheet metal carrier 92 coated with a suitable catalytic precious metal material. The catalytic coated carrier 92 is formed into a hollow cylinder 93 defining a fuel gas accommodating bore 94 extending therethrough. A tab portion 95 is formed from the catalytic coated carrier 92 and is bent inwardly to extend into the gas accommodating bore 94. A thermal mass 96 comprising a screw 97 and a nut 98 is secured to the tab portion 95 for maintaining the tab portion 95 at or above the ignition temperature of the gas catalytic combustion element 19 during periods of fuel gas interruption to the gas catalytic combustion element 19 resulting from control of the supply of fuel gas to the combustion chamber 18 by the temperature responsive control valve 61. Thus, in this way, when the supply of fuel gas is reinstated by the temperature responsive control valve 61, the tab portion 95, which has been maintained at or above the ignition temperature, again commences conversion of the fuel gas to heat by catalytic reaction, thereby progressively and rapidly raising the temperature of the remainder of the gas catalytic combustion element 19 to its ignition temperature.

The screw 97 of the thermal mass 96 comprises a head 99 and a threaded shank 100 which extends through the tab portion 95. The tab portion 95 is tightly clamped between the nut 98 and the head 99 of the screw 97, thereby maintaining good heat conducting engagement between the thermal mass 96 and the tab portion 95. The thermal mass 96 is located within the gas accommodating bore 94 of the cylindrical carrier 92 for minimising heat loss from the thermal mass 96 to the main housing 9. The mass of the thermal mass 96 is sized to be of sufficient mass for storing sufficient heat during periods while the gas catalytic combustion element 19 is converting fuel gas to heat so that the temperature of the thermal mass 96 remains at or above the ignition temperature of the gas catalytic combustion element for the duration of the longest period of fuel gas interruption to the combustion chamber 18 by the temperature responsive control valve 61. Thereby, the thermal mass 96 co-operates with the temperature responsive control valve 61 for preventing the tab portion 95 of the gas catalytic combustion element falling below its ignition temperature while the device 1 is operating to produce the aerosol from the tobacco in the vaporising chamber 24. Thus, once the gas catalytic combustion element 19 has been raised to its ignition temperature initially by flame combustion, the gas catalytic combustion element 19 continues to operate to convert fuel gas to heat without the need to re-ignite the gas catalytic combustion element 19 by flame combustion after each period of interruption of fuel gas to the combustion chamber resulting from the operation of the temperature responsive control valve 61, since the thermal mass 96 maintains the tab portion 95 of the gas catalytic combustion element at or above its ignition temperature during periods of fuel gas interruption to the combustion chamber 18. It is the fact that the thermal mass 96 co-operates in this way with the temperature responsive control valve 61 which permits the main housing 9 to be maintained at a temperature in the range of 130° C. to 250° C., and in turn the vaporising chamber 24 to be maintained at a temperature in the range of 130° C. to 250° C., while the gas catalytic combustion element 19 is converting fuel gas to heat at an operating temperature in the order of 800° C. to 900° C., since the gas catalytic combustion element 19 can be operated in the non-converting state for periods of relatively long duration.

A first inspection port 101 formed by bores 114 and 115 through the outer and inner side walls 14 and 15, respectively, of the main housing 9 facilitates inspection of the flame cavity 67 for inspecting a flame during initial flame combustion of the fuel gas/air mixture in the combustion chamber 18. A second inspection port 102 formed by bores 116 and 117 through the outer side wall 14 and the inner side wall 15, respectively, of the main housing 9 to the combustion chamber 18 adjacent the gas catalytic combustion element 19 facilitates inspection of the gas catalytic combustion element 19.

Returning now to the heat sink member 40 and referring in particular to FIGS. 10 and 11, the heat sink member 40 is of heat conductive material machined from a single piece of aluminium and comprises an elongated solid core member 104. A plurality of heat exchange fins 105 spaced apart longitudinally along the core member 104 extend circumferentially completely around the core member 104 and engage an inner surface 106 of the aerosol accommodating tube 37, see FIG. 4. The heat exchange fins 105 define with the core member 104 and the inner surface 106 of the aerosol accommodating tube 37 a plurality of galleries 108. Longitudinally extending slots 109 provided at the periphery of the heat exchange fins 105 communicate adjacent galleries 108 for facilitating the passage of the aerosol through the aerosol accommodating tube 37 past the heat sink member 40. In order to maximise the contact of the aerosol with the heat sink member 40, the slots 109 are spaced apart around the heat exchange fins 105, and the slots 109 of each heat exchange fin 105 are located at 180° around the periphery of the heat exchange fin 105, and are misaligned with the slots 109 of the two adjacent heat exchange fins 105 by 90°. Accordingly, the aerosol is drawn through a tortuous path defined by the galleries 108 and the slots 109 of the heat sink member 40 for cooling thereof and for facilitating condensing of tar and other undesirable vaporised constituents. An adjustable secondary air inlet port 110 comprising a pair of bores 112 and 113 radially extending through the primary side wall 25 and the secondary side wall 30, respectively, of the vaporising chamber housing 21 are located downstream of the primary air inlet port 53 for accommodating additional air into the vaporising chamber 24. The bores 112 and 113 are alignable when the plug portion 22 is fully engaged in the socket portion 20, and are aligned with each other by rotating the plug portion 22 in the socket portion 20. Additionally, when the bores 112 and 113 are aligned, the area of the orifice defined by the bores 112 and 113 is adjustable by rotating the plug portion 22 relative to the socket portion 20 to act as an adjusting means for varying the amount of air drawn through the secondary air inlet port 110. The secondary air inlet port 110 is closed by rotating the plug portion 22 relative to the socket portion 20 so that the respective bores 112 and 113 are overlaid with the primary and secondary side walls 25 and 30.

In this embodiment of the invention the entire main housing 9, the plug portion 22, the aerosol accommodating tube 37 and the mouthpiece 38, as well as the temperature responsive control valve 61 and the temperature responsive safety isolating valve 60 are all axially aligned and define respective central axes, all of which coincide with the main central axis 10 defined by the main housing 9. The body member 83 of the temperature responsive safety isolating valve 60 and the valve housing 73 of the temperature responsive control valve 61 are of cylindrical construction and the gas accommodating tube 37 is of circular transverse cross-section.

In use, with the plug portion 22 disengaged from the socket portion 20 of the vaporising chamber housing 21, tobacco to be vaporised is placed in the secondary hollow interior region 32 of the plug portion 22. The plug portion 22 is then re-engaged in the socket portion to form with the primary hollow interior region 29 the vaporising chamber 24. The tobacco may be placed in the secondary hollow interior region 32 of the plug portion 22 in loose form or in a sachet. If placed in the secondary hollow interior region 32 in a sachet, as the plug portion 22 is being engaged in the socket portion 20 and urged tightly into the primary hollow interior region 29, the heat transfer member 46 punctures the sachet, for permitting the release of the aerosol of the vaporised constituents of the tobacco when the tobacco has been heated in the vaporising chamber 24.

With the tobacco located in the vaporising chamber 24, the device 1 is ready for use. The button operated on/off valve 62 is activated for supplying fuel gas from the fuel gas reservoir 55 through the temperature responsive safety isolating valve 60 and the temperature responsive control valve 61 to the venturi mixer 64 where the fuel gas is mixed with air, and delivered through the diffuser 65 into the combustion chamber 18. The plunger 72 of the piezo-electric ignition mechanism 71 is activated for delivering a voltage to the electrode 69 to cause a spark to arc between the electrode 69 and the inner side wall 15 of the main housing 9. The fuel gas/air mixture in the combustion chamber 18 commences to burn in a flame in the flame cavity 67, thereby raising a downstream portion of the gas catalytic combustion element 19 to its ignition temperature. On reaching its ignition temperature, the gas catalytic combustion element commences to convert fuel gas to heat by catalytic reaction, thus progressively and rapidly raising the temperature of the remainder of the gas catalytic combustion element 19 to its ignition temperature, until the entire gas catalytic combustion element 19 is converting fuel gas to heat. At that stage, the flame is starved of fuel gas and is extinguished.

The gas catalytic combustion element 19 converts fuel gas to heat at an operating temperature of between 800° C. and 900° C. The temperature of the main housing 9 is rapidly raised to its operating temperature in the range of 130° C. to 250° C. by heat radiated from the gas catalytic combustion element 19. Heat conducted through the main housing 9 and through the heat transfer member 46 raises the temperature within the vaporising chamber 24, and in turn the temperature of the tobacco to a temperature in the range of 130° C. to 250° C. to produce the aerosol. Simultaneously, heat is conducted through the main housing 9 to the valve housing 73 of the temperature responsive control valve 61 and to the body member 83 of the temperature responsive safety isolating valve 60. Heat is transferred from the valve housing 73 into the bi-metal valving disc 79 of the temperature responsive control valve 61, which operates to control the supply of fuel gas to the combustion chamber 18 to maintain the temperature of the main housing 9 so that the temperature within the vaporising chamber 24 is between 130° C. and 250° C.

On the temperature in the vaporising chamber 24 reaching a temperature in the range of 130° C. to 250° C., desirable vaporisable constituents, for example, nicotine and other desirable constituents, are vaporised from the tobacco to produce the aerosol. Some tar and other undesirable components are also vaporised from the tobacco, however, by maintaining the temperature within the vaporising chamber 24 within the temperature range of 130° C. to 250° C., the amount of tar and other undesirable constituents which are vaporised from the tobacco is minimised.

A user places the mouthpiece 38 in his or her mouth and draws on the mouthpiece 38, thus drawing air through the primary air inlet 53 through the vaporising chamber 24. The aerosol from the vaporising chamber 24 is entrained in the air, and drawn along with the air through the heat sink member 40. The heat sink member 40 cools the vaporised constituents and condenses tar and other undesirable vaporised constituents from the tobacco onto the heat exchange fins 105. The user then inhales the mixture of air and aerosol. If it is desired to increase or decrease the amount of air being draw into the vaporising chamber 24, the plug portion 22 is rotated relative to the socket portion 20 for either aligning or misaligning the bores 112 and 113 of the secondary air inlet port 110, or for closing off the secondary air inlet port 110 entirely.

The device continues to operate until the on/off valve 62 has been deactivated for isolating the fuel gas from the fuel gas reservoir to the combustion chamber 18.

During operation the temperature responsive control valve 61 operates to maintain the temperature within the vaporizing chamber 24 within the temperature range 130° C. to 250° C. by varying the rate of supply of fuel gas to the combustion chamber 18 with an analogue type action, and also by periodically interrupting the supply of fuel gas to the combustion chamber 18 where necessary. During periods of interruption of fuel gas to the combustion chamber 18 resulting from temperature control by the temperature responsive control valve 61, the thermal mass 96 maintains a portion of the tab portion 95 of the gas catalytic combustion element 19 adjacent the thermal mass 96 at or above the ignition temperature of the gas catalytic combustion element 19, so that when the supply of fuel gas is reinstated, the gas catalytic combustion element 19 again commences to convert the fuel gas/air mixture to heat.

Referring now to FIGS. 19 and 20, there is illustrated waveforms representative of operating temperatures of the device 1 of FIGS. 1 to 18 when the device 1 is operating under two different conditions. In order to operate the device 1 at a desired temperature within the range of 130° C. to 250° C., the temperature responsive control valve 61 must be selected to operate the device at the desired temperature within the range of 130° C. to 250° C. To produce the temperature results of FIG. 19, the temperature responsive control valve 61 was selected to operate the device 1 with the temperature in the vaporising chamber 24 maintained at approximately 164° C. To produce the temperature results of FIG. 20, the temperature responsive control valve 61 was selected to operate the device 1 with the temperature in the vaporising chamber 24 maintained at approximately 220° C.

In FIGS. 19 and 20 temperature is plotted on the Y-axis in ° C., and time is plotted on the X-axis in seconds. The waveform A in both FIGS. 19 and 20 is representative of the temperature of the main housing 9 of the device 1 adjacent the combustion chamber 18. The waveform B in both FIGS. 19 and 20 is representative of the temperature of the heat transfer member 46 within the vaporising chamber 24 of the device 1, and thus this temperature of the heat transfer member 46 is a relatively accurate representation of the value of the temperature within the vaporising chamber 24. The waveform C in both FIGS. 19 and 20 is representative of the temperature of the exhaust gases exiting through the exhaust gas ports 45 from the exhaust gas chamber 42 of the device 1.

As can be seen from FIG. 19, when the temperature responsive control valve 61 is selected to operate the device 1 with the temperature in the vaporising chamber at approximately 164° C., the temperature of the heat transfer member 46, after an initial excursion to 190° C. after start-up, settles at a steady state temperature, which fluctuates between 160° C. approximately and 168° C. approximately. Accordingly, during steady state operation of the device 1, the temperature in the vaporising chamber 24 is maintained at approximately 164° C.±4° C. From start-up the temperature of the heat transfer member 46 rises to approximately 190° C. before settling at the steady state temperature of 164° C.±4° C. The temperature of the main housing 9 rises to approximately 175° C., before settling at a steady state operating temperature of approximately 166° C.±4° C. The initial heating up of the device 1 from start-up until steady state operating conditions have been reached takes approximately 120 seconds, in other words, approximately two minutes. The exhaust gas temperature exiting the exhaust gas ports 45 during the initial period after start-up rises to approximately 155° C., and then settles to a steady state temperature of approximately 125° C. ±15° C.

As can be seen from FIG. 20, when the temperature responsive control valve 61 is selected to operate the device with the vaporising chamber 24 at a temperature of approximately 220° C. The device 1 from start-up takes approximately 120 seconds to reach steady state operating conditions. Initially the temperature of the main housing 9 reaches a temperature of approximately 230° C. and then settles back to a steady state operating temperature of approximately 225° C.±3° C. The temperature of the heat transfer member 46 initially rises to a temperature of approximately 240° C. before settling back to a steady state operating temperature of approximately 220° C.±3° C. Thus, the temperature within the vaporising chamber 24 is maintained at a steady state operating temperature of approximately 220° C.±3° C. The temperature of the exhaust gas exiting through the exhaust gas ports 45 initially reaches a temperature of approximately 215° C., falling back to a temperature of approximately 120° C. before settling at an average steady state temperature of approximately 175° C.±10° C.

Accordingly, by appropriately selecting the temperature responsive control valve 61, the device 1 can be operated at any desired temperature. While, in general, the temperature responsive control valve will be selected to operate the device 1 at steady state operating temperatures in the vaporising chamber 24 at temperatures within the range of 130° C. to 250° C., it is envisaged, in certain cases, that the temperature responsive control valve may be selected to control the device at higher or lower temperatures, and the temperature at which the temperature responsive control valve is selected to control the device will be determined by the matter being vaporised in the vaporising chamber to form the aerosol. Indeed, it will be appreciated that the temperature responsive control valve 61 may be selected to operate the device 1 at steady state operating temperatures in the vaporising chamber 24 at temperatures considerably higher than 250° C., for example, at temperatures of up to 400° C., and even higher, depending on the matter to be vaporised to form the aerosol.

It will also be understood that the thermal mass 96 will be selected for maintaining the tab portion 95 of the gas catalytic combustion element 19 at or above the ignition temperature of the gas catalytic combustion element for periods during temperature interruption resulting from control of the temperature of the device by the temperature responsive control valve 61. Thus, the thermal mass will be matched with and will co-operate with the temperature responsive control valve. Indeed, as can be seen from FIGS. 19 and 20, when the temperature responsive control valve 61 is selected to operate the device with the temperature in the vaporising chamber 24 at the lower steady state operating temperature of 164° C., the periods during which the fuel gas is interrupted to the gas catalytic combustion element 19 are longer than the periods during which the fuel gas is interrupted to the gas catalytic combustion element 19 when the temperature responsive control valve is selected to operate the device with a steady state operating temperature in the vaporising chamber 24 of approximately 220° C. The durations of the periods during which the fuel gas is interrupted to the combustion chamber 18 can be determined from the time periods during which the temperatures of the waveforms A, B and C fall from their peak value to their minimum value before commencing to rise. From FIG. 19 it can be seen that the average duration of the periods during which the fuel gas is interrupted to the gas catalytic combustion element 19 when the device is operating at a steady state operating temperature in the vaporising chamber 24 of approximately 164° C. is approximately twelve seconds, while from FIG. 20 the average duration of the periods of fuel gas interruption to the gas catalytic combustion element 19 when the device is operating at a steady state operating temperature in the vaporising chamber 24 of approximately 220° C. is approximately eight seconds.

Accordingly, the higher the steady state operating temperature in the vaporising chamber 24 at which the device 1 is operated, the shorter will be the duration of the periods of fuel gas interruption to the gas catalytic combustion element 19 caused by the temperature responsive control valve 61.

Referring now to FIGS. 21 to 23, there is illustrated a portion of a device according to another embodiment of the invention, indicated generally by the reference numeral 120, for vaporising tobacco to produce an inhaleable aerosol. The device 120 is partly similar to the device 1 and similar components are identified by the same reference numerals. The main difference between the device 120 and the device 1 is that the device 120 is electrically powered by a battery 121. The device 120 comprises a main housing 122 which is located within a casing (not shown) which is substantially similar to the casing 3. The battery 121 for powering the device 120 is located in the casing 3 in a compartment in an area similar to the area in which the fuel gas reservoir 55 is located in the casing 3 of the device 1. The main housing 122 is of heat conductive material, namely, aluminium, and forms the socket portion 20 of the vaporising chamber housing 21.

A heating means for heating the tobacco in the vaporising chamber 24 to produce the aerosol comprises an electrically powered positive temperature control resistive heating element 125 which is located within and encased in the heat transfer member 46 which extends into the vaporising chamber 24. The heat transfer member 46 comprises a heat conductive shell 126 of aluminium, and the heating element 125 is in heat conductive engagement with the heat conductive shell 126 of the heat transfer member 46 for transferring heat to the tobacco. Heat is also transferred from the heating element 125 through the heat transfer member 46 into the socket portion 20 of the vaporising chamber housing 21 for heating the tobacco. An on/off switch 128 is located in the casing (not shown) for switching on and off power to the heating element 125 from the battery 121. A temperature responsive switch 129 mounted on the primary side wall 25 is responsive to the temperature of the primary side wall 25, which in turn is indicative of the temperature within the vaporising chamber 24 for controlling the supply of power from the battery 121 to the heating element 125 for maintaining the temperature within the vaporising chamber 24 at a temperature in the range of 130° C. to 250° C.

Otherwise, the device 120 is similar to the device 1, as is its use. Tobacco is placed in the secondary hollow interior region 32 of the plug portion 22 which is engaged in the socket portion 20 of the vaporising chamber housing 21 for forming the vaporising chamber 24. The on/off switch 128 is operated for applying power from the battery 121 to the heating element 125 through the temperature responsive switch 129 for powering the heating element 125, which in turn heats the tobacco to a temperature in the range of 130° C. to 250° C. The temperature is maintained within the range of 130° C. to 250° C. by the temperature responsive switch 129. When it is desired to deactivate the device 120, the on/off switch 128 is appropriately operated.

Referring now to FIG. 24, there is illustrated a portion of a device according to another embodiment of the invention, indicated generally by the reference numeral 130, for vaporising vaporisable matter to form an inhaleable aerosol. The device 130 is substantially similar to the device 1, which is described with reference to FIGS. 1 to 20, and similar components are identified by the same reference numerals. The main difference between the device 130 and the device 1 is that in this embodiment of the invention the exhaust gas chamber 42 is substantially filled with a heat conductive gauze type material, which in this embodiment of the invention is a knitted type metal fabric 131 of the type typically used in pot scrubs for scouring grease and other dirt from pots and pans. Such knitted type metal fabric material will be well known to those skilled in the art. The knitted metal fabric 131 is randomly folded and placed in the exhaust gas chamber 42. The portion 48 of the heat transfer member 46 which extends into the exhaust gas chamber 42 extends into the knitted metal fabric 131 and is in heat conductive engagement therewith. The knitted metal fabric 131 diffuses the exhaust gases from the combustion chamber 18 throughout the exhaust gas chamber 42, thereby slowing down the flow of exhaust gases and also extracting heat therefrom. The heat extracted from the exhaust gases by the knitted metal fabric 131 is transferred into the heat transfer member 46 for transferring into the vaporising chamber 24. It has been found that the inclusion of the knitted metal fabric 131 in the exhaust gas chamber 42 reduces the temperature of the exhaust gases exiting the exhaust gas ports 45, thereby significantly improving the operating efficiency of the device 130 over and above that of the device 1, and indeed, it has been found that the temperature difference between the temperature within the vaporising chamber 24 and the main housing 9 is also reduced.

Additionally, the device 130 comprises a valving means, namely, a non-return valve 132 in the primary air inlet port 53 for permitting flow of air through the primary inlet port 53 into the vaporising chamber 24 when the aerosol is being drawn from the vaporising chamber 24 through the mouthpiece 38, and for preventing reverse flow of aerosol through the primary air inlet port 53 from the vaporising chamber 24 when the aerosol is not being drawn from the vaporising chamber 24 through the mouthpiece 38. It has been found that in certain cases when the device is operated with the vaporising chamber 24 at a relatively high temperature, the aerosol formed in the vaporising chamber 24 permeates outwardly through the primary air inlet port 53 during periods when the aerosol is not being drawn through the mouthpiece 38. The provision of the non-return valve 32 in the primary air inlet port 53 prevents loss of the aerosol from the vaporising chamber 24 through the primary air inlet port 53.

Referring now to FIG. 25, there is illustrated a socket portion 140 of a vaporising chamber housing which is suitable for use with the device 1, the device 120 and 130. In this embodiment of the invention the vaporising chamber housing is substantially similar to the vaporising chamber housing 21 described with reference to the device 1, and similar components are identified by the same reference numerals. The main difference between the vaporising chamber housing of this embodiment of the invention and the vaporising chamber housing 21 is that four parallel spaced apart heat transfer members 46 extend from the primary partition wall 28 into the primary hollow interior region 29 of the socket portion 20 for transferring heat to tobacco in the vaporising chamber 24. The heat transfer members 46 are similar to the heat transfer member 46 which extends into the vaporising chamber 24 of the device 1. Otherwise, the socket portion 140 of the vaporising chamber housing is similar to the socket portion 20 of the vaporising chamber housing 21, and its use in conjunction with the plug portion 22 is similar for forming the vaporising chamber 24. Where the socket portion 140 is being used with the device 120, it is envisaged that a heating element 125, similar to that described with reference to the device 120 will be located in at least one of the heat transfer members 46, and preferably, in each of the heat transfer members 46.

While the heating means of the device 120 which has been described with reference to FIGS. 21 to 23 has been described as being provided by a positive temperature control resistive heating element, any other suit-able heating means may be provided, for example, the heating means may comprise a conventional resistive heating element, an induction heating element or any other suitable heating means. It is also envisaged that the heating means may be provided in a portion of the main housing 122 which would extend axially rearwardly from the vaporising chamber housing 21.

While the device 1 according to the invention described with reference to FIGS. 1 to 20 has been described as comprising heat transfer to the vaporising chamber by both temperature conduction through the main housing and also by heat transfer from the exhaust gases, it is envisaged in certain cases that heat transfer from the exhaust gases may be omitted.

While the device 130, which has been described with reference to FIG. 24, has been described as comprising a valving means for selectively controlling the flow of air through the primary air inlet port 53 in the form of a non-return valve, any other suitable valving means may be provided. Indeed, it is envisaged that the valving means may comprise a manually operated valving member, which would be operated by a user, and which would normally be in the closed state, closing the primary air inlet port 53, and when a user wished to draw aerosol from the vaporising chamber 24, the valving member would be manually operated into the open state by the user for permitting air to enter the vaporising chamber 24 through the primary air inlet port 53. It is also envisaged that the device 1 according to the invention, which has been described with reference to FIGS. 1 to 20, may also be provided with a suitable valving means for selectively controlling air through the primary air inlet port 53, as could the device described with reference to FIGS. 21 to 23. It is also envisaged that the device 1 according to the invention, which is described with reference to FIGS. 1 to 20, may also be provided with a heat conductive gauze material located in the exhaust gas chamber. While the heat conductive gauze material in the exhaust gas chamber described in the device 130 with reference to FIG. 24 has been described as being a knitted metal fabric of the type used in pot scrubs, any other suitable heat conductive material may be used. Indeed, in certain cases, it is envisaged that heat exchange fins may be provided extending from the main housing into the exhaust gas chamber for transferring heat from the exhaust gases into the body member, and in turn to the vaporising chamber. Such heat exchange fins could be arranged to form a tortuous passageway for the gas for slowing the exhaust gases passing through the exhaust gas passageway.

While the thermal mass has been described as comprising a nut and screw, any other suitable thermal mass may be used, for example, a rivet, and indeed, in certain cases, it is envisaged that a portion of the gas catalytic combustion element may be of mass sufficient for maintaining that portion of the gas catalytic combustion element at or above its ignition temperature for periods of fuel gas interruption. For example, if the gas catalytic combustion element were provided as a ceramic gas catalytic combustion element, the thermal mass of portions of the ceramic gas catalytic combustion element may be sufficient for maintaining those portions of the gas catalytic combustion element at or above the ignition temperature of the gas catalytic combustion element for periods of fuel gas interruption.

While the device 1 according to the invention described with reference to FIGS. 1 to 20 has been described as comprising a secondary air inlet which is adjustable, it is envisaged that the secondary air inlet may be dispensed with. It is also envisaged in certain cases that the portion of the heat transfer member located within the vaporising chamber 24 and the air inlet chamber 51 may be provided with air ducts for accommodating air through the heat transfer member from the air inlet chamber 51 to the vaporising chamber for heating the air in the heat transfer member as it is drawn from the air inlet chamber 51 to the vaporising chamber 24.

While the gas catalytic combustion element has been described as comprising a perforated sheet metal carrier having a precious metal catalyst material coated thereon, any other suitable gas catalytic combustion element may be used, and where the gas catalytic combustion element is provided with a sheet metal carrier, it is not essential that the sheet metal carrier be perforated. The gas catalytic combustion element may also be provided with a mesh or gauze carrier appropriately coated with a catalyst material. Needless to say, in certain cases, it is envisaged that the gas catalytic combustion element may be a ceramic gas catalytic combustion element.

Additionally, it will be appreciated that while the vaporising chamber housing 21 has been described as being formed as an integral part of the main housing 9 which also forms the combustion chamber housing 17 of the device 1, it is envisaged, in certain cases, that the vaporising chamber housing and the combustion chamber housing may be formed separately, but would be in heat conducting engagement with each other either directly or through a heat conducting member.

While the devices according to the invention have been described with a specific type of temperature control valve for controlling the flow of fuel gas to the combustion chamber, any other suitable temperature control valve may be used. For example, in certain cases it is envisaged that a temperature control valve comprising a self-latching relay of the type disclosed in PCT Published Application Specification No. WO 95/09712.

It is also envisaged that a filter may be provided in the aerosol accommodating tube either upstream or downstream of the heat sink member for filtering the aerosol being drawn therethrough. Such a filter may be of the type commonly used in filter tipped cigarettes, or any other suitable filter for filtering the aerosol from the vaporising chamber. Indeed, in certain cases, such a filter may be used instead of the heat sink member.

While the devices according to the invention have been described for producing an aerosol from tobacco, it is envisaged that the device may be adapted for producing an aerosol from any other vaporisable matter, such as any other vaporisable herb or plant matter, or a vaporisable medicinal compound or the like, and where the device is used for vaporising matter other than tobacco, the device will be adapted for operating with the steady state temperature in the vaporising chamber maintained at an appropriate temperature for the matter being vaporised.

While the main housing, the temperature responsive control valve and the temperature responsive isolating valve have been described as being of aluminium material, they may be of any other suitable heat conducting material, for example, brass, stainless steel, copper or the like.

While a particular type of heat sink means has been described for locating in the aerosol accommodating tube between the vaporising chamber and the mouthpiece, any other suitable heat sink means could be provided. For example, in certain cases, it is envisaged that the heat sink means may be provided in the form of a porous sintered filter, a gauze filter, which typically would be of metal gauze material, or any other suitable material suitable for cooling the aerosol to an acceptable mouth-feel temperature, and for condensing any steam or water vapour in the aerosol.

While the heat transfer means have been described as comprising a heat transfer member extending into the vaporising chamber, any other suitable heat transfer means may be provided, and while the heat transfer member or members have been described as being of a particular material, the heat transfer member or members may be of any other suitable material. It is also envisaged that in the case of electrically powered devices, it is not essential that the heating means be located in the heat transfer member.

It will be appreciated that where the devices according to the invention are provided for vaporising vaporisable matter in tobacco, the tobacco may be placed in the vaporising chamber in any suitable form, whether flake, granular, solid, particulate, or any desirable form.

Additionally, while the devices have been described as being operable within a temperature range of 130° C. to 250° C., it will be readily apparent to those skilled in the art that the devices according to the invention may be operated at any desired temperature, either below 130° C. or above 250° C., and indeed, in certain cases, the devices may be operable at relatively high temperatures up to and above 400° C., and even up to and above 500° C., and the operating temperatures will largely depend on the matter being vaporised.

The invention claimed is:

1. A device for vaporizing vaporizable matter, the device comprising:
   a combustion chamber housing defining a combustion chamber,
   a gas catalytic combustion element located in the combustion chamber for converting fuel gas to heat for heating the combustion chamber housing, the gas catalytic combustion element comprising a carrier coated with a catalytic precious metal material,
   a vaporizing chamber housing defining a vaporizing chamber for the vaporizable matter, the vaporizing chamber housing being in heat conducting relationship with the combustion chamber housing for transfer of heat thereto from the combustion chamber housing for heating the vaporizable matter in the vaporizing chamber,
   a temperature responsive control valve responsive to a temperature indicative of the temperature of the vaporizing chamber for controlling the supply of fuel gas to the combustion chamber to maintain the temperature within the vaporizing chamber at a vaporization temperature of a vaporizable constituent of the vaporizable matter for producing an aerosol thereof, and
   a thermal mass in heat conducting engagement with a portion of the gas catalytic combustion element and being matched with and co-operating with the temperature responsive control valve for maintaining the portion of the gas catalytic combustion element at a temperature at or above the ignition temperature of the gas catalytic combustion element while fuel gas to the combustion chamber is isolated therefrom by the temperature responsive control valve, the thermal mass being located within the gas catalytic combustion element and being spaced apart from the combustion chamber housing for minimising heat transfer from the thermal mass to the combustion chamber housing.

2. A device as claimed in claim 1 in which a mouthpiece communicating with the vaporizing chamber facilitates drawing of the aerosol from the vaporizing chamber.

3. A device as claimed in claim 1 in which a heat transfer member of heat conductive material extends into the vaporizing chamber for transferring heat into the vaporizing chamber.

4. A device as claimed in claim 3 in which the heat transfer member tapers towards its distal end.

5. A device as claimed in claim 3 in which an exhaust gas chamber is located between the vaporizing chamber and the combustion chamber, the exhaust gas chamber communicating with the combustion chamber for receiving exhaust gases therefrom, and being isolated from the vaporizing chamber by a heat exchange means for preventing exhaust gases entering the vaporizing chamber from the exhaust gas chamber and for transferring heat from the exhaust gases to the vaporizing chamber.

6. A device as claimed in claim 5 in which the heat exchange means is formed by a primary partition wall of heat conductive material located between the vaporizing chamber and the exhaust gas chamber.

7. A device as claimed in claim 6 in which the combustion chamber housing and a portion of the vaporizing chamber housing are formed from a main housing of heat conductive material.

8. A device as claimed in claim 7 in which an aerosol outlet port is provided from the vaporizing chamber for accommodating aerosol therefrom.

9. A device as claimed in claim 1 in which a temperature responsive safety isolation valve is provided for isolating the combustion chamber from fuel gas in the event of the temperature of the combustion chamber housing exceeding a predetermined safe maximum temperature.

10. A device as claimed in claim 1 in which the gas catalytic combustion element is located in the combustion chamber for defining with the combustion chamber a flame cavity for facilitating initial ignition of fuel gas in the flame cavity in a flame for raising the temperature of the gas catalytic combustion element to its ignition temperature, and an ignition means is provided to the flame cavity for igniting the fuel gas to burn in a flame in the flame cavity.

11. A device as claimed in claim 1 in which the temperature responsive control valve comprises a heat conductive valve housing defining a valve chamber, the heat conductive valve housing being in heat conducting relationship with the vaporizing chamber housing, a bi-metal valving member located in the valve chamber and co-operating with one of a valve inlet and a valve outlet to the valve chamber for controlling the flow of fuel gas through the valve chamber in response to the temperature of the vaporizing chamber housing.

12. A device as claimed in claim 1 in which the device is adapted for vaporizing vaporizable constituents in tobacco.

13. A device as claimed in claim 1 in which the thermal mass is formed separate of the gas catalytic combustion element.

14. A device as claimed in claim 1 in which a tab shaped portion of the gas catalytic combustion element extends from the gas catalytic combustion element into a fuel gas passageway defined by the gas catalytic combustion element, and the thermal mass is located on and in heat conductive engagement with the tab shaped portion.

15. A device as claimed in claim 14 in which the gas catalytic combustion element is of sleeve shape construction having a hollow core for forming the fuel gas passageway for accommodating fuel gas therethrough, and the tab shaped portion of the gas catalytic combustion element extends into the hollow core.

16. A device as claimed in claim 6 in which the heat transfer member extends from the primary partition wall into the vaporizing chamber.

17. A device as claimed in claim 7 in which the vaporizing chamber housing comprises a socket portion and a hollow plug portion, the hollow plug portion being releasably engageable with the socket portion for defining the vaporizing chamber.

18. A device as claimed in claim 17 in which the socket portion is formed by the primary partition wall and a primary side wall extending around the primary partition wall defining with the primary partition wall a primary hollow interior region to form the socket portion, and the plug portion comprises an end cap and a secondary side wall extending around the end cap and defining therewith a secondary hollow interior region, the respective primary and secondary side walls forming respective open mouths to the respective primary and secondary hollow interior regions for facilitating communicating therebetween for forming the vaporizing chamber.

19. A device as claimed in claim 18 in which the secondary side wall of the plug portion is releasably engageable with the primary side wall of the socket portion.

20. A device as claimed in claim 17 in which the socket portion of the vaporizing chamber is formed by the main housing.

21. A device as claimed in claim 11 in which the bi-metal valving member is of the type which transitions from one state to another, which are mirror images of each other, as the temperature of the bi-metal valving member transitions across a predetermined transition temperature, and the bi-metal valving member is constrained within the valve chamber to prevent transitioning of the bi-metal valving member between the respective states, so that the control of the flow of fuel gas through the temperature responsive control valve is analogue.

* * * * *